(12) United States Patent
Manor et al.

(10) Patent No.: US 12,029,594 B2
(45) Date of Patent: Jul. 9, 2024

(54) SYSTEMS AND METHODS FOR ENHANCED IMAGING AND ANALYSIS

(71) Applicant: THE SALK INSTITUTE FOR BIOLOGICAL STUDIES, La Jolla, CA (US)

(72) Inventors: Uri Manor, La Jolla, CA (US); Linjing Fang, La Jolla, CA (US)

(73) Assignee: THE SALK INSTITUTE FOR BIOLOGICAL STUDIES, A CORPORATION OF CALIFORNIA, La Jolla, CA (US)

( * ) Notice: Subject to any disclaimer, the term of this patent is extended or adjusted under 35 U.S.C. 154(b) by 439 days.

(21) Appl. No.: 17/269,986

(22) PCT Filed: Aug. 21, 2019

(86) PCT No.: PCT/US2019/047570
§ 371 (c)(1),
(2) Date: Feb. 19, 2021

(87) PCT Pub. No.: WO2020/041517
PCT Pub. Date: Feb. 27, 2020

(65) Prior Publication Data
US 2021/0321963 A1    Oct. 21, 2021

Related U.S. Application Data

(60) Provisional application No. 62/720,762, filed on Aug. 21, 2018.

(51) Int. Cl.
*A61B 6/42* (2024.01)
*A61B 6/00* (2006.01)
(Continued)

(52) U.S. Cl.
CPC .......... *A61B 6/4258* (2013.01); *A61B 6/4035* (2013.01); *A61B 6/5282* (2013.01);
(Continued)

(58) Field of Classification Search
CPC .......................... A61B 6/4258; A61B 6/4035
See application file for complete search history.

(56) References Cited

U.S. PATENT DOCUMENTS

| | | | |
|---|---|---|---|
| 8,350,933 B2 * | 1/2013 | Fattal | G06T 5/003 348/241 |
| 2005/0190816 A1 * | 9/2005 | Simeon | G01K 13/02 374/E13.006 |

(Continued)

*Primary Examiner* — Yi Yang
(74) *Attorney, Agent, or Firm* — Norton Rose Fulbright US LLC

(57) ABSTRACT

A method to, is provided for collecting an image from a sample. The method includes selecting a radiation level for a first probe to meet a desired radiation dosage, and providing, with the first probe, a radiation at a selected point within a region of the sample. The method includes identifying a second selected point within the region of the sample based on a down sampling scheme, and providing a second radiation amount at the second selected point within the region of the sample. The method also includes interpolating a first datum and a second datum based on an up sampling scheme to obtain a plurality of data, and forming an image of the region of the sample with the plurality of data. A system to perform the above method and including the first probe is also provided.

19 Claims, 32 Drawing Sheets

(51) Int. Cl.
*A61B 6/40* (2024.01)
*G06T 11/00* (2006.01)

(52) U.S. Cl.
CPC ............ *A61B 6/5288* (2013.01); *A61B 6/542* (2013.01); *G06T 11/00* (2013.01); *G06T 2210/41* (2013.01)

(56) References Cited

U.S. PATENT DOCUMENTS

| | | | |
|---|---|---|---|
| 2009/0283682 A1* | 11/2009 | Star-Lack | A61B 6/5235 250/363.1 |
| 2010/0303384 A1* | 12/2010 | Knee | G06T 3/4023 382/298 |
| 2011/0026593 A1* | 2/2011 | New | H04N 19/18 375/E7.243 |
| 2013/0208129 A1* | 8/2013 | Stenman | G06T 5/002 348/207.1 |
| 2013/0238201 A1* | 9/2013 | Redden | G06V 10/255 701/50 |
| 2014/0240952 A1* | 8/2014 | Nakanishi | H01S 5/02253 29/25.01 |
| 2015/0338475 A1* | 11/2015 | Overweg | G01R 33/58 324/309 |
| 2016/0203944 A1* | 7/2016 | Ominami | H01J 37/16 250/310 |
| 2017/0085872 A1* | 3/2017 | Perron | H04N 19/117 |
| 2018/0317861 A1* | 11/2018 | Sun | A61B 6/037 |
| 2019/0333623 A1* | 10/2019 | Hibbard | A61N 5/1039 |
| 2019/0348256 A1* | 11/2019 | Geurts | G06T 7/254 |
| 2020/0016428 A1* | 1/2020 | Verhaegen | A61N 5/1002 |

* cited by examiner

600A

600B

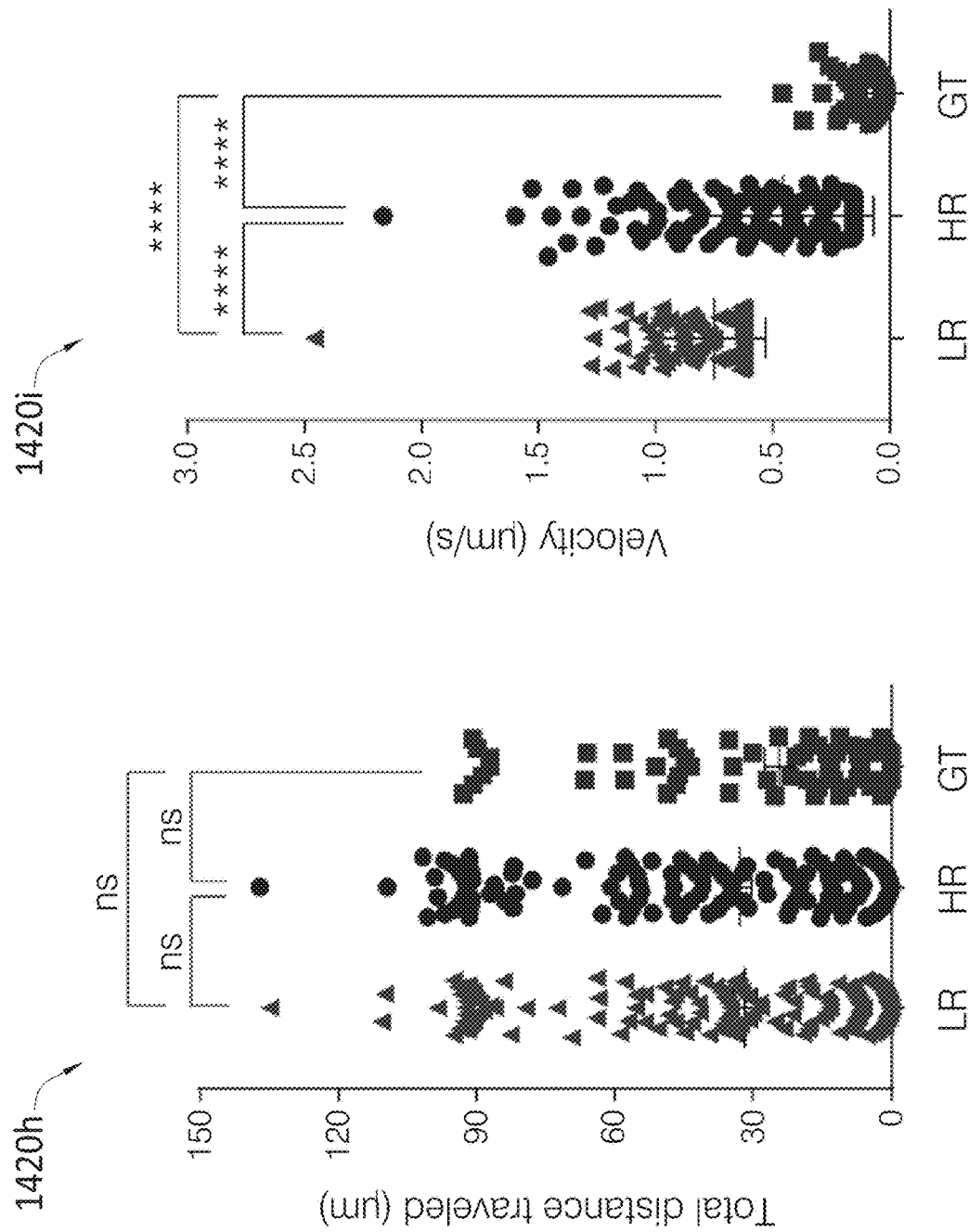

SYSTEMS AND METHODS FOR ENHANCED IMAGING AND ANALYSIS

CROSS-REFERENCE TO RELATED APPLICATIONS

The present application is a U.S. National Stage patent application of International Patent Application No. PCT/US2019/047570, filed on Aug. 21, 2019, which claims the benefit of U.S. Provisional Application No. 62/720,762 filed Aug. 21, 2018, the benefit of which is claimed and the disclosures of which are incorporated herein by reference in their entireties.

ACKNOWLEDGMENT OF GOVERNMENT SUPPORT

This invention was made with government support under NIH CA014195 awarded by the National Institutes of Health. The government has certain rights in the invention.

BACKGROUND

Field

The embodiments disclosed herein are generally directed towards systems and methods for enhancing imaging analysis. More specifically, embodiments disclosed herein are directed to the use of non-linear image processing algorithms to produce enhanced images on the back end of an imaging system, thus relaxing the constraints for the image collection hardware and procedures.

Description of Related Art

Current imaging instrumentation has evolved substantially with the availability of powerful devices, e.g., lasers, electron beams, and other high-resolution, high-energy radiation sources (e.g., X-rays, isotope radiation) and more sensitive detectors having multi-channel detection capabilities. In many instances, the acquisition of the high-resolution images that such devices allow involves long scanning times and exposure of the subject sample to potential radiation damage and other undesirable alterations (drift, heating, and temperature gradients). Additionally, implementing high-resolution imaging at the front end of the instrumentation (e.g., via hardware for probing and detection) typically reduces the time resolution of the imaging protocol, compared to a lower resolution image obtained with the same hardware (e.g., at a coarser scanning rate). It is desirable to apply image-enhancing techniques on the back end of the imaging system to relax the interaction between probe and detector with the sample, while maintaining or improving the image quality.

SUMMARY

In a first embodiment, a method for collecting an image from a sample includes selecting a radiation level for a first probe to meet a desired radiation dosage, and providing, with the first probe, a first radiation amount at a first selected point within a region of the sample, based on the radiation level. The method also includes associating the first selected point with at least the portion of a first emitted radiation resulting from an interaction of the first radiation amount with the sample, to form a first datum, identifying a second selected point within the region of the sample based on a down sampling scheme, and providing, with the first probe, a second radiation amount at the second selected point within the region of the sample. The method also includes associating the second selected point with at least the portion of a second emitted radiation resulting from the interaction of the second radiation amount with the sample, to form a second datum and interpolating the first datum and the second datum based on an up sampling scheme to obtain at least a third datum. The method also includes obtaining a plurality of data from multiple selected points in a portion of the region of the sample and forming an image of the region of the sample with the plurality of data.

In a second embodiment, a system for collecting an image from a sample includes a first probe configured to deliver a radiation to a selected point in the sample, and a first detector configured to measure a scattered radiation resulting from an interaction between the radiation and the sample. The system also includes a memory storing instructions and one or more processors configured to execute the instructions and to cause the system to select a radiation level for a first probe to meet a desired radiation dosage. The one or more processors also cause the system to provide, with the first probe, a first radiation amount at a first selected point within a region of the sample, based on the radiation level, and to associate the first selected point with at least the portion of a first emitted radiation resulting from an interaction of the first radiation amount with the sample, to form a first datum. The one or more processors also cause the system to identify a second selected point within the region of the sample based on a down sampling scheme, to provide, with a first probe, a second radiation amount at the second selected point within the region of the sample and to associate the second selected point with at least the portion of a second emitted radiation resulting from the interaction of the second radiation amount with the sample, to form a second datum. The one or more processors also cause the system to interpolate the first datum and the second datum based on an up sampling scheme to obtain at least a third datum, to obtain a plurality of data from multiple selected points in a portion of the region of the sample, and to form an image of the region of the sample with the plurality of data.

In yet other embodiment, a computer-implemented method to train an algorithm for collecting an image of a sample includes retrieving a high-resolution image of a known sample and identifying a first classifier for the high-resolution image of the known sample, wherein the first classifier includes a first value. The computer-implemented method also includes aggregating, with a selected coefficient, one or more pixels in the high-resolution image to obtain a low-resolution image of the sample, wherein the one or more pixels are selected based on a desired down sampling of an image collection system, and obtaining a second classifier for the low-resolution image of the sample, wherein the second classifier includes a second value. The computer-implemented method also includes determining a metric value with a difference between the second value and the first value and modifying the selected coefficient.

BRIEF DESCRIPTION OF FIGURES

FIGS. 14A through 14K illustrate some applications of the neural network in confocal fluorescence microscopy, according to various embodiments.

Figure 1:
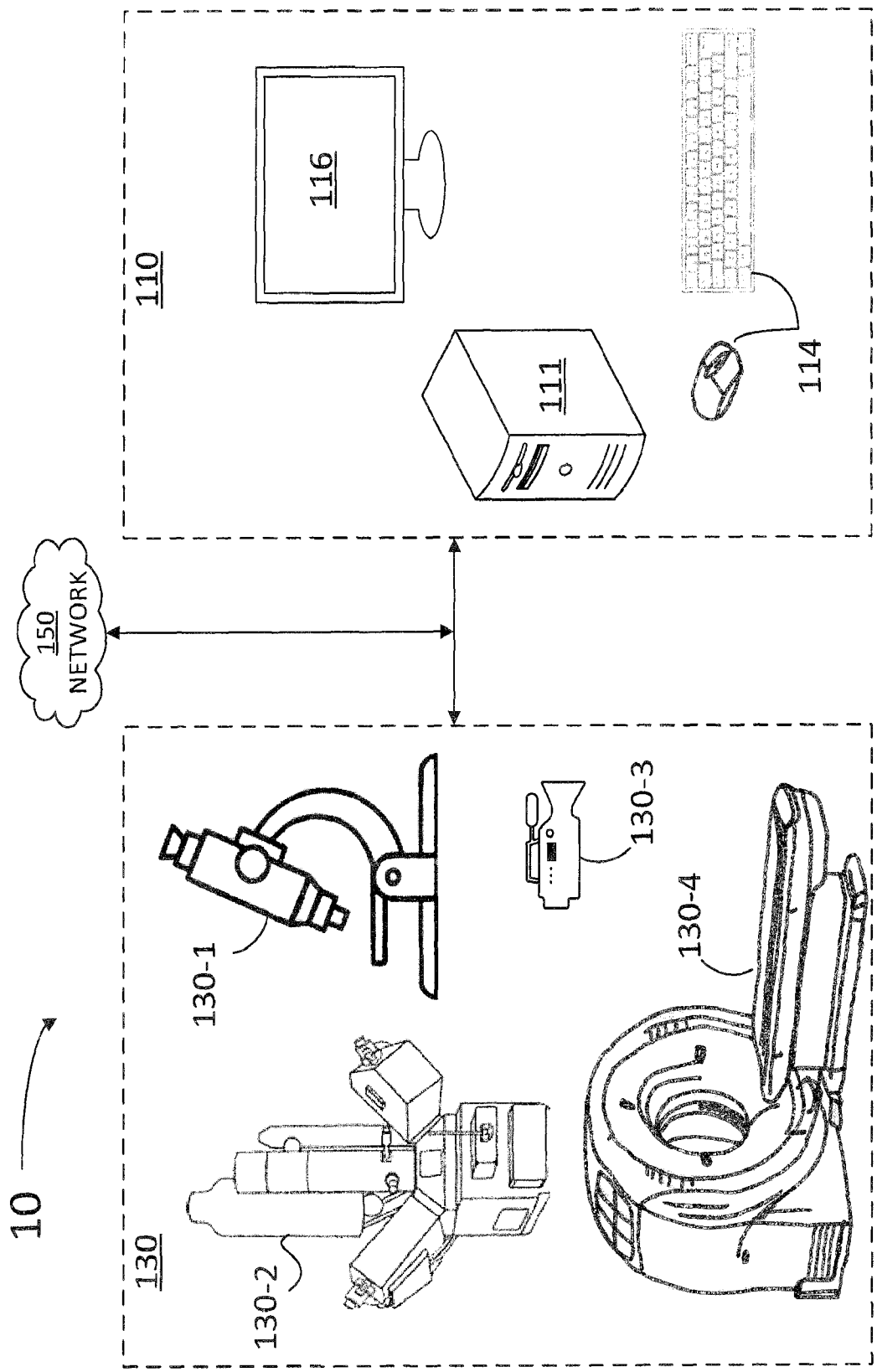
FIG. 1 illustrates an architecture including imaging instrumentation and associated control devices for enhanced imaging, according to various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

This specification describes various exemplary embodiments of systems, methods, and software for enhanced novelty detection. The disclosure, however, is not limited to these exemplary embodiments and applications or to the manner in which the exemplary embodiments and applications operate or are described herein.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular.

As used herein, the terms "comprise," "comprises," "comprising," "contain," "contains," "containing," "have," "having," "include," "includes," and "including" and their variants are not intended to be limiting, are inclusive or open-ended and do not exclude additional, unrecited additives, components, integers, elements, or method steps. For example, a process, method, system, composition, kit, or apparatus that includes a list of features is not necessarily limited only to those features but may include other features not expressly listed or inherent to such process, method, system, composition, kit, or apparatus.

In accordance with various embodiments herein, the systems, methods, and software are described for high-resolution cellular and tissue imaging, including point scanning imaging systems combined with microscopy. Point scanning imaging systems in embodiments consistent with the present disclosure may include a scanning electron microscope (SEM) or a scanning transmission electron microscope (STEM), an ion-based imaging system or a high-resolution cryoSTEM. In some embodiments, a point scanning imaging system includes a laser scanning confocal microscope, or a fluorescence microscope, and the like.

For imaging systems, it is desirable to optimize resolution, speed, illumination intensity, and signal-to-noise ratio (SNR). For point scanning systems, optimizing all of the above simultaneously is a challenging task. State-of-the-art systems typically incur in undesirable compromises between the above factors. In some configurations, point scanning systems are constrained by the fact that higher resolution imaging requires a higher number of pixels for proper sampling, resulting in a direct relationship between imaging time and pixel resolution. In addition, the increased imaging time results in a higher dose of radiation transferred to the sample, for imaging. The higher dose may be deleterious to the measure from direct damage to the sample (e.g., alter the physiology or the nature of the sample) and from thermal drifts and heating that may result from the radiation.

Similar to SEM, laser scanning confocal microscopy also suffers from a direct relationship between pixel resolution and sample damage (e.g., phototoxicity/photobleaching). This can be a major barrier for cell biologists who wish to study the dynamics of smaller structures such as mitochondria, which regularly undergo fission and fusion, but also show increased fission and swelling in response to phototoxicity. In extreme cases, phototoxicity can cause cell death, which is incompatible with live cell imaging (data not shown). HR scanning confocal microscopy also suffers from the direct relationship between pixel resolution and imaging time, making live cell imaging of faster processes challenging (e.g., organelle motility in neurons).

Embodiments as disclosed herein mitigate the challenges described above by combining a low-resolution hardware approach (e.g., less invasive, less costly, and faster) with an enhanced data processing software to recover the desired high resolution. In some embodiments, the solutions disclosed herein can overcome the above limitations by implementing a solution in the field of computer technology, namely the use of point-scanning super-resolution (PSSR) models to compensate for the hardware limitations of an imaging system. In some embodiments, PSSR is implemented with deep-learning algorithms, neural network algorithms, or artificial intelligence algorithms that are trained against a large stock of previously collected and stored high-resolution images. In some embodiments, the high-resolution images are oversampled, "ground truth," images acquired on scanning transmission electron (STEM) or laser scanning confocal microscopes. In some embodiments, high-resolution images are used to generate semi-synthetic training data for creating PSSR models. The PSSR models are then used to restore (e.g., upgrade or enhance) under sampled images. In some embodiments, the PSSR models disclosed herein may restore under sampled images acquired with different optics, detectors, samples, or sample preparation methods, relative to the training data sets.

The ability to restore or enhance under sampled images enables the acquisition of previously unattainable resolution and SNR datasets with standard scanning imaging systems. This broadens the range and capabilities of the scanning imaging systems into new and challenging applications. Accordingly, PSSR models as disclosed herein provide a highly practical and versatile strategy for point scanning imaging with optimal resolution, speed, and sensitivity.

For example, in the case of a laser scanning confocal fluorescence microscope, the higher speeds enabled by under sampled images combined with PSSR models as disclosed herein facilitates otherwise unattainable spatiotemporal resolution. This may be used to study physiological phenomena such as mitochondrial dynamics for prolonged periods of time with reduced phototoxicity or photobleaching. In addition to phototoxicity issues, the slow speed of HR scanning confocal imaging results in temporal under sampling of fast-moving structures such as motile mitochondria in neurons. Accordingly, in some embodiments, a PSSR model as disclosed herein may provide sufficient restoration of under sampled time-lapse-imaging of mitochondrial trafficking in neurons, or fission or fusion events.

In some embodiments, PSSR models as disclosed herein may be used for image analysis and segmentation by using segmentation atlases or maps trained into the PSSR model before image collection. For example, in some embodiments, a PSSR model as disclosed herein may be used for subcellular structure segmentation (e.g., identifying cellular organelles and the like), and to segment images with higher resolution and capture finer details. In some embodiments, PSSR models as disclosed herein are configured to increase the SNR of an image by removing noise components (e.g., "denoising") and sources that may be trained into the PSSR model prior to image collection. In some embodiments, a PSSR model as disclosed herein may be trained to correlate high-resolution images collected with one or more imaging techniques (e.g., light microscopy and EM). Accordingly, in some embodiments, a PSSR model may enhance an EM image of a region of a sample to a higher resolution based on a corresponding region of the sample captured by fluorescence microscopy. Moreover, in some embodiments, a PSSR model as disclosed herein may be trained to convolve images of the same region of a sample collected with different techniques (and different resolution) into a single, comprehensive image of the region of the sample. Additionally, in some embodiments, the PSSR model may be able to deconvolve a high-resolution image into components corresponding to different scanning imaging techniques (e.g., able to deconvolve to both EM and light microscopic images from a single high-resolution image).

Embodiments as disclosed herein include PSSR models that are capable of restoring images under sampled by a factor, f, which can be 2, 3, or even larger (e.g., 10, 16, 20, or more). Accordingly, a deep learning-based image facilitates faster, lower dose imaging (e.g., lower electron radiation for SEM and lower photon dosage for scanning confocal microscopy) by about the same factor, f. This provides a technical advantage for the imaging system in terms of reduced sample damage, and reduced raw image file sizes that are buffered out of the system, e.g., via a network link (wireless or wired). Accordingly, PSSR models as disclosed herein provide a strategy for increasing the spatiotemporal resolution of point scanning imaging systems at the back end, to previously unattainable levels, well beyond hardware limitations at the front end (e.g., sample damage or imaging speed).

In embodiments including electron microscopy, methods and devices as disclosed herein may provide significant advantages. Three-dimensional electron microscopy (3DEM) is a powerful technique for determining the volumetric ultrastructure of tissues, which is desirable for connectomics analysis of samples. In addition to serial section EM (ssEM) and focused ion beam SEM (FIB-SEM), one of the most common tools for high throughput 3DEM imaging is serial blockface scanning electron microscopy (SBFSEM), wherein a built-in ultramicrotome iteratively cuts ultrathin sections (usually between 50-100 nm) off the surface of a blockface after it was imaged with a scanning electron probe. This method facilitates relatively automated, high-throughput 3DEM imaging with minimal post-acquisition image alignment. It is desirable to avoid higher electron doses, as these cause sample charging, which renders the sample too soft to section and to image reliably. Furthermore, high-resolution 3DEM of relatively large volumes typically implies long imaging times and large file sizes and presents a significant bottleneck for many labs. Thus, embodiments as disclosed herein include acquiring 3DEM datasets with sub-Nyquist sampling (e.g., pixel sizes ≥4 nm), and post-processing the resulting image to enhance the resolution to a desirable level using the model in the image processing engine. Increasing the resolution of the down sampled collection enables the reliable detection or analysis of smaller subcellular structures, such as presynaptic vesicles. Accordingly, embodiments as disclosed herein capture targeted regions of large (and maybe low-resolution) datasets for higher resolution ultrastructural information. Thus, the ability to computationally increase the resolution of these datasets is of high value to avoid sample damage and provide rapid image collection times and protocols.

FIG. 1 illustrates an architecture 10 including imaging instrumentation 130-1 (a light microscope), 130-2 (an electron/ion microscope), 130-3 (a video camera), and 130-4 (a magnetic resonance imaging system—MRI—). Hereinafter, light microscope 130-1, electron/ion microscope 130-2, video camera 130-3, and MRI 130-4 will be collectively referred to as "imaging instrumentation 130"). As described herein, light microscope 130-1 may include any instrument using optical imaging technology, such as laser scanned fluorescence, confocal fluorescence, Raman spectroscopy, atomic spectroscopy, laser induced fluorescence, and the like. Electron/ion microscope 130-2 may include a SEM, a TEM, a STEM, or an ion-based imaging device. Imaging instrumentation 130 includes hardware such as optical components, electron guns, and other electronic components and detectors to manipulate the hardware and interact with a sample to generate imaging data. Accordingly, in some embodiments, imaging instrumentation 130 includes a point-scanning system configured to form an image of a sample region by collecting data point by data point for a plurality of points in a region of the sample. Imaging instrumentation 130 performs a point scanning of the image region based on scanning parameters, including spatial resolution (or "slide"), radiation dosage, and dwell time. The resolution is the distance between two neighboring data points in the sample. The radiation dosage is the amount of energy flux transmitted to each point in the sample, for imaging. The dwell time is the amount of time spent on each data point, including the delivering of the radiation, and the collection of a scattered radiation from the sample.

Architecture 10 also includes one or more associated control devices 110 for enhanced imaging, according to various embodiments. Control device 110 may include a computer, a display for displaying an output image, and input devices such as a keyboard, a mouse, and a stylus or pointer. Control device 110 may be configured to provide commands and instructions to manipulate the hardware in imaging instrumentation 130. Imaging instrumentation 130 provides the imaging data from the sample to control device 110. The data is transmitted to control device 110 to generate an image on display 116. The data may also be stored in a memory of computer 111. The memory of computer 111 may also include a PSSR model having instructions which, when executed by computer 111, cause the computer to process the data from imaging instrumentation 130 to generate an image in display 116.

In some embodiments, the PSSR model may be used by computer 111 to perform data analysis in real time, as imaging instrumentation 130 is collecting an image, and provide instructions and commands, accordingly. For example, in some embodiments, the PSSR model may be configured to identify a blood vessel or an intracellular structure as an image is being collected, and computer 111 may direct imaging instrumentation 130 to scan the sample along the predicted path of the blood vessel, or to focus and zoom-in on the intracellular structure. Furthermore, in some embodiments, the PSSR model may determine, based on a plurality of collected data points but before finalizing a scan of a portion of a sample region, a change in one or more scanning parameters, based on a predicted image quality of the portion of the sample region.

In some embodiments, architecture 10 may include a network 150 to which control device 110 and imaging instrumentation 130 may be communicatively coupled. In some embodiments, control device and imaging instrumentation 130 may be remotely located from one another, and may use network 150 to communicate with each other. In that regard, network 150 may be a private network, or a public network (such as the world wide web), and may be implemented as a local area network (LAN) or a wide area network (WLAN). Further, control device 110 and imaging instrumentation 130 may communicate with network 150 via a wired communication channel (e.g., telephone, Ethernet, or cable) or a wireless communication channel (e.g., via a Wi-Fi or Bluetooth connection, and the like). In some embodiments, control device 110 may include input devices 114 (e.g., a mouse, a keyboard, and the like).

Figure 2:
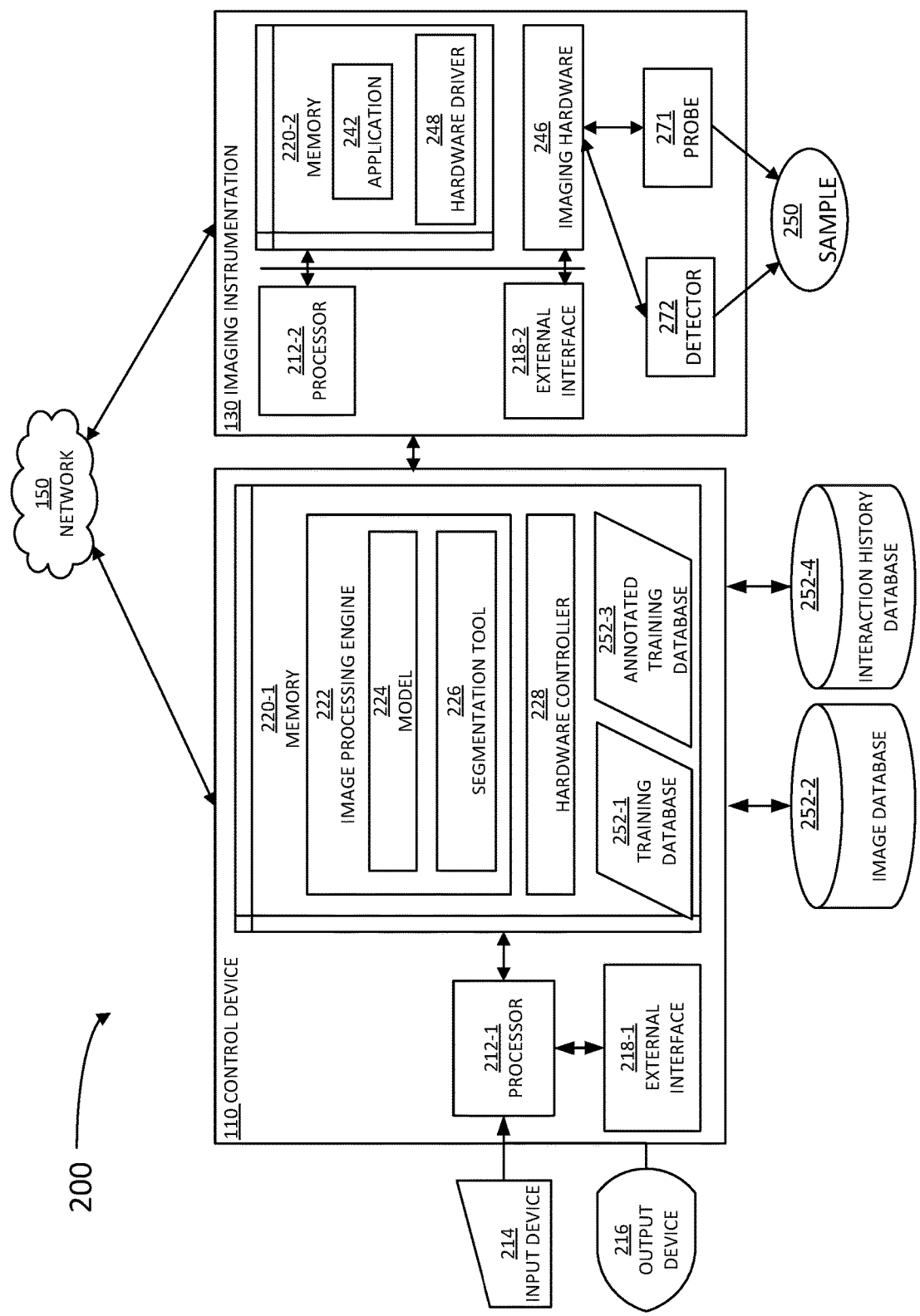
FIG. 2 illustrates a detailed block diagram of a system in the architecture of FIG. 1, according to various embodiments.

FIG. 2 illustrates a detailed block diagram of a system 200 in architecture 10, according to various embodiments. System 200 includes control device 110 and imaging instrumentation 130 (cf. FIG. 1) communicatively coupled with each other via external interfaces 218-1 and 218-2 (hereinafter, collectively referred to as "external interfaces 218"), respectively. External interfaces 218 may include wireless communication components, e.g., radio-frequency (RF) antennas and radios, or wired components (e.g., copper wires, fiber optics, and the like). Accordingly, external interfaces 218 may include hardware such as RF circuits, amplifiers, modulators and filters, and also software such as digital processing software and the like. External interfaces 218 may also be configured to communicate with network 150 via a wired or a wireless communication protocol (cf. FIG. 1). In some embodiments, as described above, control device 110 and imaging instrumentation 130 may be remotely located from one another, and external interfaces 218 may communicate with one another via network 150.

Imaging instrumentation may include a memory 220-2 storing instructions, and a processor 212-2 configured to execute the instructions and cause imaging instrumentation to perform at least one or more of the steps in methods consistent with the present disclosure. For example, processor 212-2 may cause imaging instrumentation 130 to collect an image from a sample 250. In that regard, the instructions in memory 220-2 may be included in an application 242 for image collection and processing, and in a hardware driver 248, configured to provide commands to an imaging hardware 246. Imaging hardware includes electronic, mechanical, and optical components that enable a probe 271 and a detector 272 to interact with sample 250. In some embodiments, probe 271 is configured to deliver a radiation to a selected point in sample 250, and detector 272 is configured to measure a scattered radiation resulting from the interaction between the radiation and sample 250.

In some embodiments, control device 110 includes a memory 220-1 storing instructions, and a processor 212-1. Memory 220-1 may include an image processing engine 222 and a hardware controller 228. Image processing engine 222 may include a model 224 (e.g., a PSSR model) and a segmentation tool 226. In some embodiments, model 224 may include deconvolution algorithms such as structured illumination microscopy, single-molecule localization microscopy (SMLM), and pixel reassignment microscopy. In some embodiments, image processing engine 222 may configure imaging instrumentation 130 according to a pre-selected post-processing strategy. The power of image processing engine 222 presents a new opportunity for redesigning imaging instrumentation 130 and substantially reduces costs while extracting meaningful imaging data. Similarly, image processing engine 222 may be configured to perform automated, real-time corrections to the images and real-time feedback to the imaging hardware 246.

Hardware controller 228 is configured to provide instructions to and receive status information from hardware driver 248 via external interfaces 218. In some embodiments, hardware controller 228 communicates with image processing engine 222 to provide data from an image collection scan from imaging instrumentation 130. In some embodiments, hardware controller 228 may receive instructions from image processing engine 222 to adjust or modify scanning parameters for imaging instrumentation 130. Processors 212-1 and 212-2 will be collectively referred to, hereinafter, as "processors 212." Likewise, memories 220-1 and 220-2 will be collectively referred to, hereinafter, as "memories 220."

One or more of processors 212 is configured to execute the instructions and to cause system 200 to direct probe 271 to a first selected point within a region of sample 250. One or more of processors 212 also causes system 200 to select a radiation rate for probe 271 based on a desired radiation dosage, to provide the radiation at the first selected point, based on the radiation rate, to collect at least a portion of the scattered radiation from the first selected point with detector 272, and to associate the first selected point with the portion of the scattered radiation to form a first datum.

In some embodiments, input image 301 may include an array of pixel values. These pixel values, depending on the image resolution and size, may be an array of numbers corresponding to (length)×(width)×(number of channels). The number of channels can also be referred to as the 'depth.' For example, the array could be L×W×Red Green Blue color model (RGB values). The RGB would be considered three channels, each channel representing one of the three colors in the RGB color model. In some embodiments, system 200 may characterize a 20×20 image with a representative array of 20×20×3 (for RGB), with each point in the array assigned a value (e.g., 0 to 255) representing pixel intensity. A datum may include the point of the array and the assigned value or values (e.g., RGB values) for that point. Given this array of values, image processing engine 222 obtains numbers indicating a probability of the image being a certain class (e.g., 0.80 for 'cell,' 0.15 for 'cell wall,' and 0.05 for 'no cell,' or 'interstitial').

One or more of processors 212 also causes system 200 to direct probe 271 to a second selected point within the region of sample 250 to form a second datum based on a down sampling scheme stored in memory 220-1. In some embodiments, the down sampling scheme is provided by model 224, which is trained with previously collected images stored in a training database 252-1. More generally, model 224 may include any algorithm (linear and non-linear) trained to provide a simple answer based on a complex input. Accordingly, the simple answer may be the down sampling scheme, and the complex input of multiple data points collected from sample 250 during a current scanning session, or a previous scanning session, or from a previously collected image. In that regard, model 224 may include an artificial intelligence algorithm, a machine learning algorithm, a deep learning algorithm, a neural network (NN), a convolutional neural network (CNN, U-Net, and the like), a generative adversarial neural network (GAN), a residual neural network (ResNet), or any combination of the above.

In some embodiments, training database 252-1 includes images from a larger universe of images stored in an image database 252-2. Memory 220-1 may also store an annotated training database 252-3, which includes captions and other textual descriptions of the images stored in training database 252-1. Annotated training database 252-3 may include an image classification value associated with each image in training database 252-1. An image classification value may include a class or a probability of classes that best describes an image (e.g., as in a caption, wherein each word or phrase has a specific code or value). Accordingly, and with the training from databases 252-1 and 252-2, image processing engine 222 may be configured to identify objects of interest within an image in a database or provided by imaging instrumentation 130, with a high level of accuracy using model 224, and segmentation tool 226.

In some embodiments, there is a direct, one-to-one correspondence between images in training database 252-1 and entries in annotated training database 252-3. In some embodiments, training database 252-1 and annotated training database 252-3 are embedded into one training database. In addition to image database 252-2, or in conjunction with it, some embodiments may include an interaction history database 252-4. Interaction history database 252-4 may include, in addition to previously collected images, metadata associated with the collection of the images. The metadata may include the technique used for image collection (e.g., SEM, STEM, confocal fluorescence, magnetic resonance, PET, and the like), scanning parameters (e.g., pixel resolution, dwell time, radiation dosage, and the like), image classification values and descriptors, and sample-related information (e.g., biological or physiological descriptions of the region of the sample being imaged). Hereinafter, image database 252-2 and interaction history database 252-4 will be collectively referred to as "databases 252." In that regard, images and data from databases 252 may be collected by different imaging instrumentation, and from different samples, at different locations and times. In some embodiments, at least one of databases 252 may be remotely located from control device 110. In such case, control device 110 may access one or more of databases 252 through external interface 218-1, through network 150. Accordingly, model 224 may be trained using training data collected from any one of databases 252, training database 252-1, and annotated training database 252-3, to better predict an image quality from data being collected by imaging instrumentation 130 in real time, or after a full scan of sample 250 (or a region thereof) has been completed.

One or more of processors 212 also causes system 200 to interpolate the first datum and the second datum based on a reverse of the down sampling scheme to obtain at least a third datum. In some embodiments, the third datum (e.g., the interpolation of the first datum and the second datum) may be provided by model 224 or by segmentation tool 226. Further, one or more of processors 212 also causes system 200 to repeat the preceding steps to cover a plurality of data from multiple selected points in a portion of the region of sample 250, and to form an image of the region of the sample with the plurality of data, using image processing engine 222. Control device 110 may also include an input device 214 and an output device 216 (e.g., input devices 114 and display 116, cf. FIG. 1).

Figure 3:
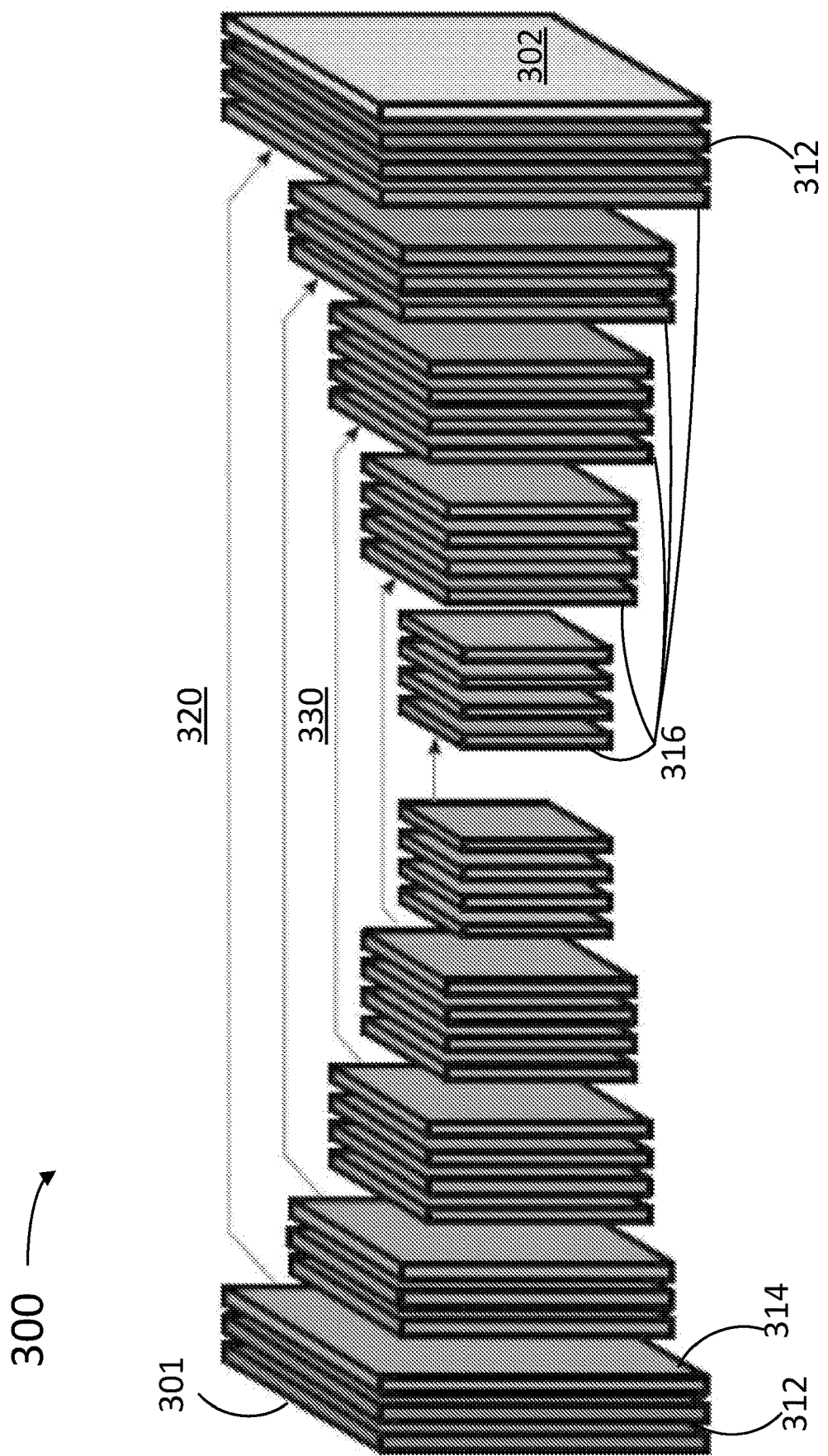
FIG. 3 illustrates a block diagram of a convolutional neural network for enhanced imaging, according to various embodiments.

FIG. 3 illustrates a block diagram of a convolutional neural network (CNN) 300 for enhanced imaging, according to various embodiments. In some embodiments, CNN 300 may be included in an algorithm, or may be combined with a segmentation tool, as described above (e.g., model 224 and segmentation tool 226, cf. FIG. 2). In some embodiments, CNN 300 takes an input image 301 having a first resolution (e.g., number of pixels, quality, and SNR), and generates an output image 302 having a second resolution. More specifically, in some embodiments, CNN 300 is configured so that the second resolution is higher than the first resolution (e.g., by a factor of less than 10, a factor of 10, or even higher). The image quality may be a single value indicative of image resolution, SNR, and other values generally associated with image quality such as sharpness, contrast, color range, blur, and the like. In some embodiments, the image quality of output image 302 is higher than the image quality of input image 301 by a factor of less than 10, a factor of 10, or more.

In some embodiments, CNN 300 may include a single-frame neural network. In some embodiments, CNN 300 may include a ResNet-based U-Net for training (e.g., training model 224, cf. FIG. 2) and/or a GAN.

Figure 4:
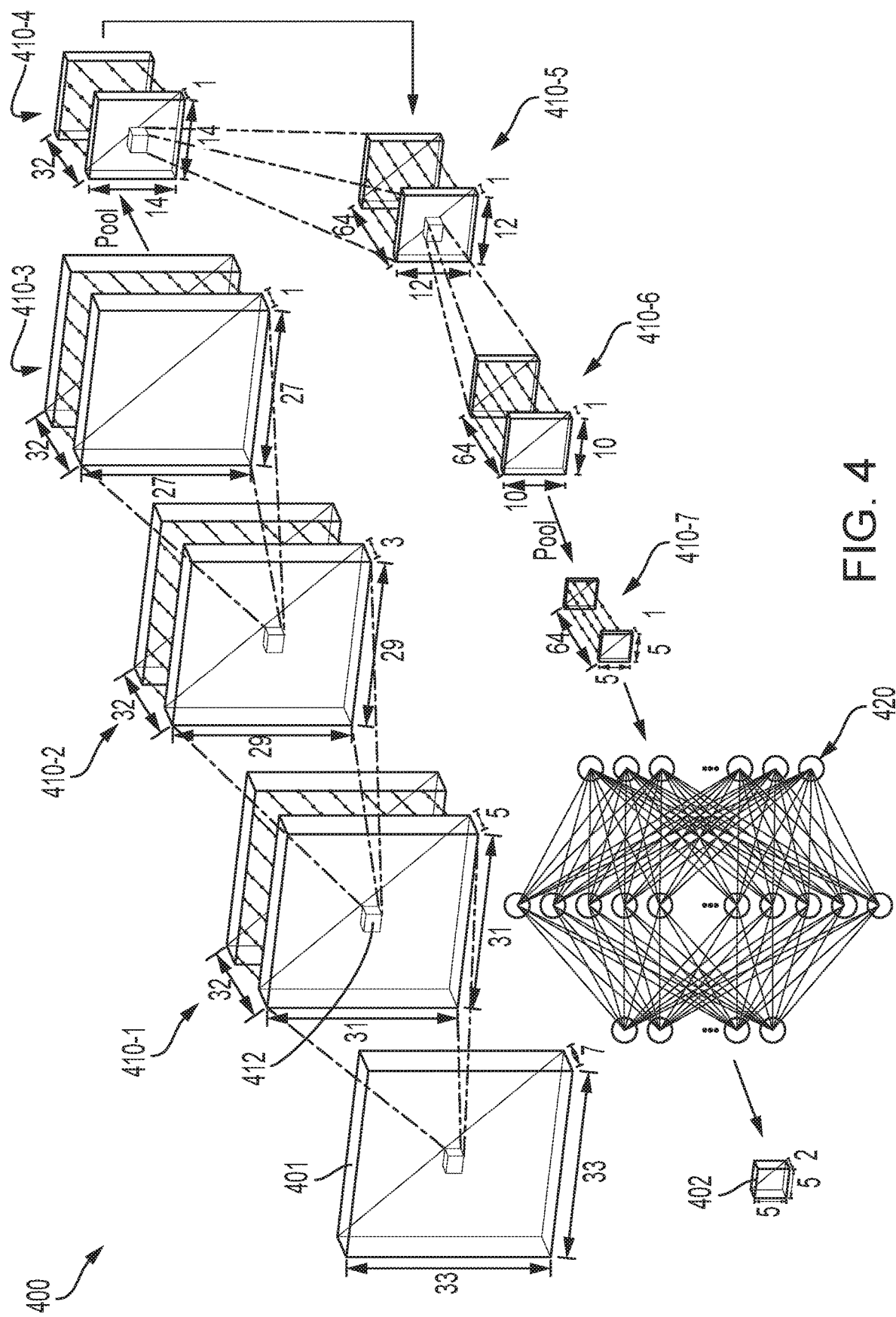
FIG. 4 illustrates a detailed block diagram of a convolutional neural network for enhanced imaging, according to various embodiments.

FIG. 4 illustrates a detailed block diagram of a CNN 400 for enhanced imaging, according to various embodiments. In some embodiments, CNN 400 generally accomplishes an advanced form of image processing and classification/detection by first looking for low level features such as, for example, edges and curves, and then advancing to more abstract (e.g., unique to the type of images being classified) concepts through a series of convolutional layers 410-1, 410-2, 410-3, 410-4, 410-5, 410-6, and 410-7 (hereinafter, collectively referred to as "convolutional layers 410"). CNN 400 passes an input image 401 through a series of convolutional, non-linear, pooling (or down sampling, as will be discussed in more detail below), and fully connected layers (e.g., layers 410), and get an output 402. In some embodiments, output 402 may be a single class or a probability of classes that best describes the image or detects objects on the image, or a full image having a higher (or different) pixel count, a higher resolution, or a higher quality. In some embodiments, CNN 400 includes a stack of distinct layers 410 that transform input image 401 into output image 402 (e.g., holding the class scores) through a differentiable function. Input image 401 may be a volume (e.g., a three-dimensional—3D—object) wherein each datum is a 'voxel.' Likewise, output 402 may be a volume formed by a plurality of voxels.

In some embodiments, layer 410-1 may be a convolutional layer (Conv) configured to process representative arrays of input image 401 using a series of parameters. Rather than processing input image 401 as a whole, CNN 400 analyzes a collection of image sub-sets 412 using a filter (or 'neuron' or 'kernel'). Sub-sets 412 (or 'regions') may include a focal point in the array, as well as surrounding points. For example, a filter can examine a series of 2×2 areas (or regions) in a 33×33 image. Regions 412 can be referred to as receptive fields. Since the filter generally will possess the same depth as the input, an image with dimensions of 33×33×7 would have a filter of the same depth (e.g., 2×2×7). The actual step of convolving, using the exemplary dimensions above, would involve sliding the filter along the input image, multiplying filter values with the original pixel values of the image to compute element wise multiplications, and summing these values to arrive at a single number for that examined region of the image.

After completion of this convolving step, using a 2×2×2 filter, an activation map (or filter map) having dimensions of 31×31×5 will result. For each additional layer used, spatial dimensions are better preserved such that using 32 filters will result in 32 layers 410-1 (generically referred to as 'activation maps 410') of 31×31×5 pixels. Each filter will generally have a unique feature it represents (e.g., colors, edges, curves, and the like) that, together, represent the feature identifiers required for the final image output. These filters, when used in combination, allow CNN 400 to process input image 401 to detect those features present at each pixel. Therefore, if a filter serves as a curve detector, the convolving of the filter along input image 401 produces an array of numbers in the activation map that correspond to 'high likelihood' of a curve (high summed element wise multiplications), 'low likelihood' of a curve (low summed element wise multiplications), or a zero value at points where input image 401 includes no curve. As such, the greater number of filters (also referred to as channels) in the Conv, the more depth (or data) that is provided on activation map 410, and therefore more information about the input that will lead to a more accurate output. In some embodiments, the outputs of layers 410 are tiled so that their input regions overlap, to obtain a better representation of input image 401. Tiling of layers 410 may be repeated for every such layer to allow CNNs to tolerate translation of the input image 401.

Balanced with accuracy of CNN 400 is the processing time and power needed to produce a result. In other words, the more filters (or channels) used, the more time and processing power needed to execute the Conv. Therefore, the choice and number of filters (or channels) to meet the desired image enhancement in output 402 may be selected in view of the computational time and power available. To further enable a CNN to detect more complex features, additional Convs can be added to analyze outputs from the previous Conv (e.g., activation maps 410). For example, if a first Conv looks for a basic feature such as a curve or an edge, a second Conv (e.g., layer 410-2, 410-3 through 410-7) can look for a more complex feature such as shapes, which can be a combination of individual features detected in an earlier Conv layer (e.g., 410-1, 410-2 through 410-7).

By providing a series of Convs, CNN 400 can detect increasingly higher-level features to eventually arrive at a probability of detecting a complex object (e.g., mitochondria, a blood vessel, a plant root, a neuronal dendrite, and the like). Moreover, as the Convs stack on top of each other, analyzing the previous activation map output 410, each Conv in the stack is naturally going to analyze a larger and larger receptive field, by virtue of the scaling down that occurs at each Conv level, thereby allowing CNN 400 to respond to a growing region of pixel space in detecting the object of interest.

CNN 400 includes a group of processing blocks, including at least one processing block for convoluting input image 401 and at least one for deconvolution (or transpose convolution). Additionally, the processing blocks can include at least one pooling block in convolutional layer 410-4 and unpooling block 420 (e.g., pooling layers 314 and up sampling layers 312, cf. FIG. 3). Pooling block 410-4 can be used to scale down an image in resolution to produce an output available for Conv. This can provide computational efficiency (e.g., less time and less power usage), which can in turn improve actual performance of CNN 400. Pooling, or sub sampling, enables blocks to keep filters small and computational requirements reasonable. In some embodiments, pooling block 410-4 may coarsen output 402 (e.g., reducing spatial information within a receptive field), reducing it from the size of the input by a specific factor. Unpooling blocks 420 can be used to reconstruct these coarse outputs to produce output 402 with the same dimensions as input 401. Unpooling block 420 may include a reverse operation of a convoluting block to return an activation output to the original input volume dimension.

However, the unpooling process generally just simply enlarges the coarse outputs into a sparse activation map. To avoid this result, the deconvolution block densifies this sparse activation map to produce both an enlarged and dense activation map that eventually, after any further necessary processing, output 402 has size and density much closer to input 401. As a reverse operation of the convolution block, rather than reducing multiple array points in the receptive field to a single number, the deconvolution block associates a single activation output point with multiple outputs to enlarge and densify the resulting activation output.

It should be noted that while pooling blocks can be used to scale down an image and unpooling blocks can be used to enlarge these scaled down activation maps, convolution and deconvolution blocks can be structured to both convolve/deconvolve and scale down/enlarge without the need for separate pooling and unpooling blocks.

A processing block can include other layers that are packaged with a convolutional or deconvolutional layer. These can include, for example, a ReLU or exponential linear unit layer (ELU), which are activation functions that examine the output from a Conv in its processing block. The ReLU or ELU layer acts as a gating function to advance only those values corresponding to positive detection of the feature of interest unique to the Conv.

According to embodiments as disclosed herein, CNN 400 avoids the lost spatial information from pooling layer 410-4 and reduces/minimizes internal covariate shifts inherent in a back-propagation process. Further, CNN 400 reduces processing time between input image 401 and output 402, which is desirable to achieve more complex feature detection in image processing engines as disclosed herein.

In some embodiments, CNN 400 includes combinations of convolutional and fully connected layers, with pointwise nonlinearity applied at the end of or after each layer. A convolution operation on small regions of input image 401 may be introduced to reduce the number of free parameters and improve generalization. In some embodiments, layers 410 in CNN 400 may share weight parameters. Accordingly, the same filter (weights bank) may be used for each pixel in the layer, which reduces memory footprint and improves performance.

In some embodiments, training of CNN 400 includes applying a progressive resizing technique. The progressive resizing technique includes two rounds of training with HR images scaled to xy pixel sizes of 256×256 and 512×512 and LR images scaled to 64×64 and 128×128 progressively (e.g., for SEM or STEM imaging instrumentation). The first round is initiated with a pretrained ResU-Net, and CNN 400 trained from the first round served as the pre-trained model for the second round. The intuition behind this is it quickly reduces the training loss by allowing the model to see many images at a small scale during the early stages of training. As the training progresses, CNN 400 focuses more on picking up high-frequency features reflected through fine details that are only stored within larger scale images. Therefore, features that are scale-variant can be recognized through the progressively resized learning at each scale.

Testing images for training CNN 400 may be cropped into smaller tiles before being fed into the model due to the memory limit of graphic cards.

Figure 5:
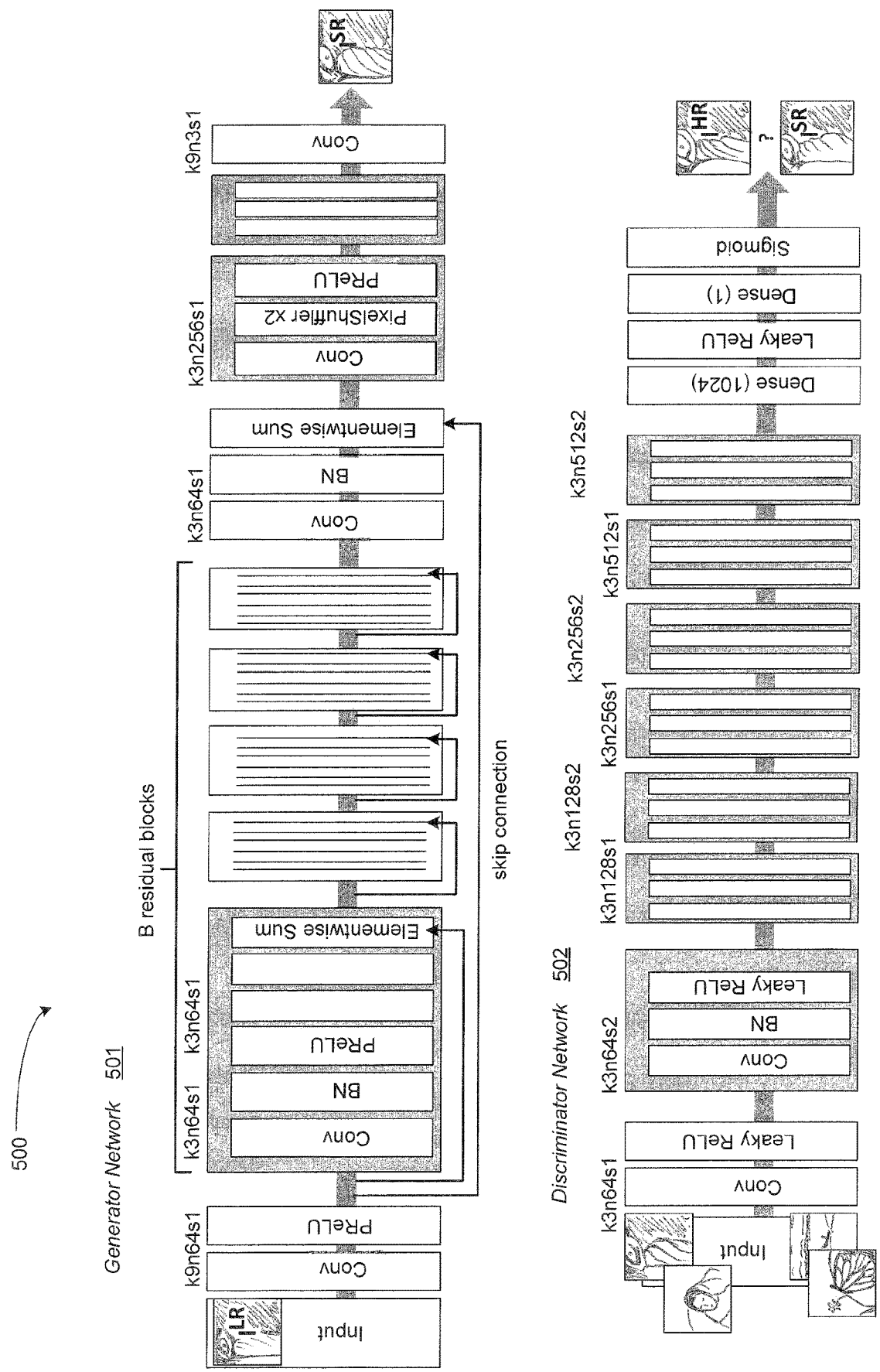
FIG. 5 illustrates a block diagram of a generative adversarial network for enhanced imaging, according to various embodiments.

FIG. 5 illustrates a block diagram of a generative adversarial network (GAN) 500 for enhanced imaging, according to various embodiments. GAN 500 includes a generator network 501 competing with a discriminator network 502. Generator network 501 adjusts its coefficients to create high-resolution synthetic images, while discriminator network 502 adjusts its coefficients to distinguish the synthetic images created by generator network 501 versus high-resolution images originally obtained with an imaging instrumentation (e.g., imaging instrumentation 130, cf. FIGS. 1 and 2). In some embodiments, GAN 500 may be referred to as a super-resolution GAN (SRGAN). The architecture of GAN 500 with corresponding kernel size (k), number of feature maps (n), and stride (s) is indicated in the figure for each convolutional layer.

Figure 6A:
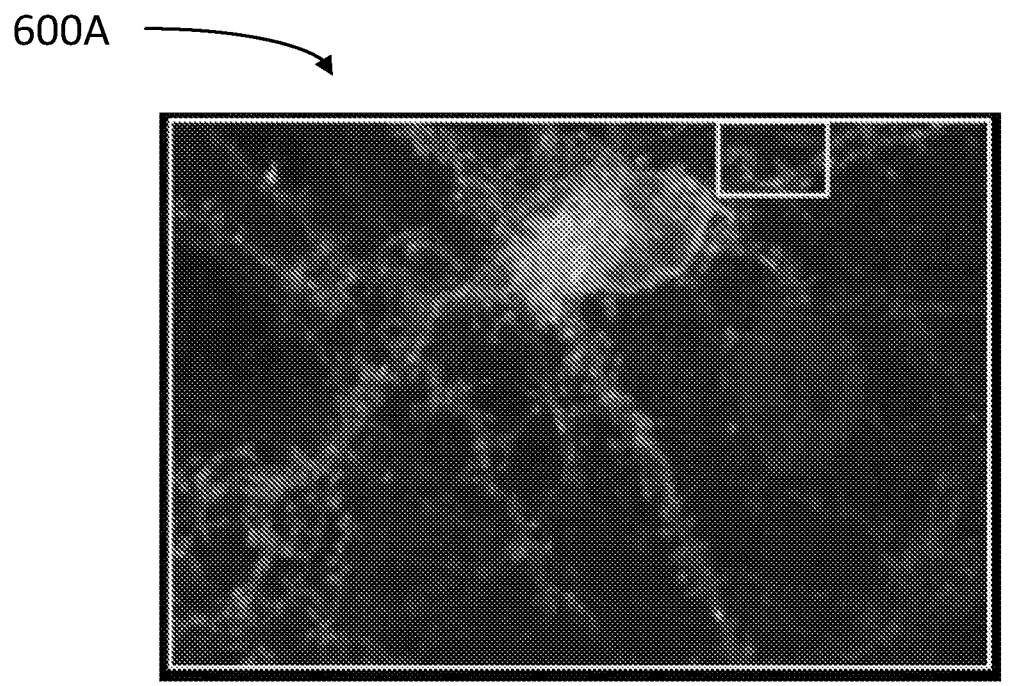
FIGS. 6A and 6B illustrate an image enhancement of a neuron obtained, according to various embodiments.
Figure 6B:
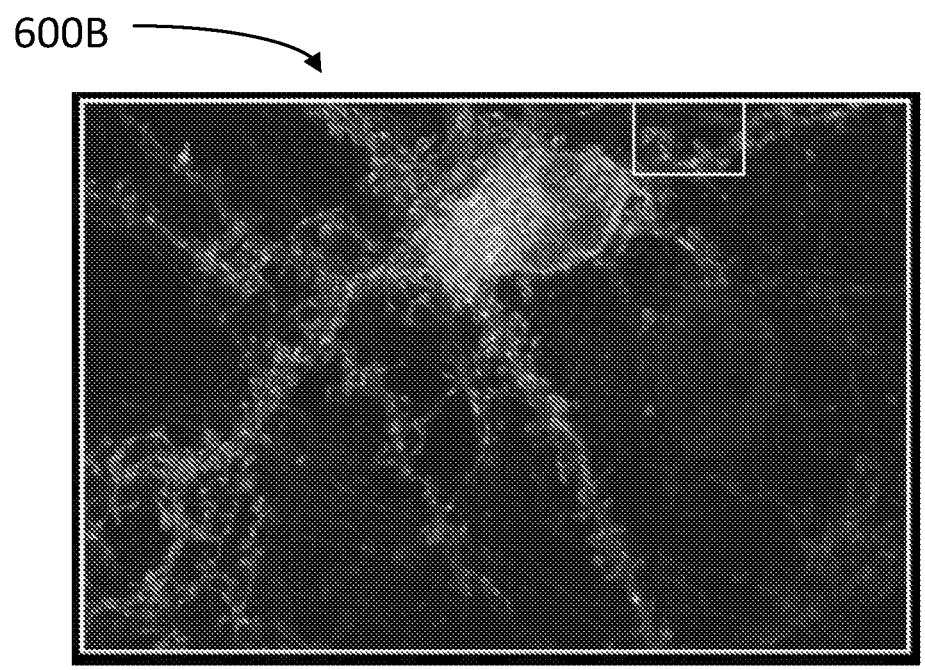

FIGS. 6A and 6B illustrate an image enhancement of a neuron obtained, according to various embodiments. The images shown may be collected using an imaging instrumentation communicatively coupled with a control device, as disclosed herein (e.g., control device 110 and imaging instrumentation 130, cf. FIGS. 1 and 2). The imaging instrumentation is a confocal microscope, and the sample is a neuronal network.

FIG. 6A illustrates a low-resolution (LR) RGB image (225*150 pixels) 600A generated by a 4× manual down sampling of a 'ground truth' image (GT). The GT image may be a 'gold standard,' high-resolution (HR) image obtained using the same imaging instrumentation or the same technique. In some embodiments, the GT image may be obtained using a different imaging instrumentation, or even a different technique (e.g., SEM, STEM, and the like).

FIG. 6B illustrates an up sampled high-resolution (HR) RGB image 600B generated by a model in an image processing engine in the control device (e.g., model 224, cf. FIG. 2) when LR image 600A is provided as the input (900×600 pixels). Images 600A and 600B will be collectively referred to, hereinafter, as "images 600."

FIGS. 7A through 7D illustrate image enhancements on a portion of the images 600 obtained according to various embodiments. Images 700A, 700B, 700C, and 700D will be collectively referred to, hereinafter, as "images 700." Images 700 show detailed comparisons of the same region cropped from images 600. The image enhancement in images 700 may be obtained with an image processing engine and a model in the control device (e.g., image processing engine 222 and model 224, cf. FIG. 2).

Figure 7A:
FIGS. 7A through 7D illustrate image enhancements on a portion of the image in FIGS. 6A-6B obtained, according to various embodiments.

FIG. 7A illustrates image 700A, which is the region cropped from LR image 600A (30*20 pixels).

Figure 7B:
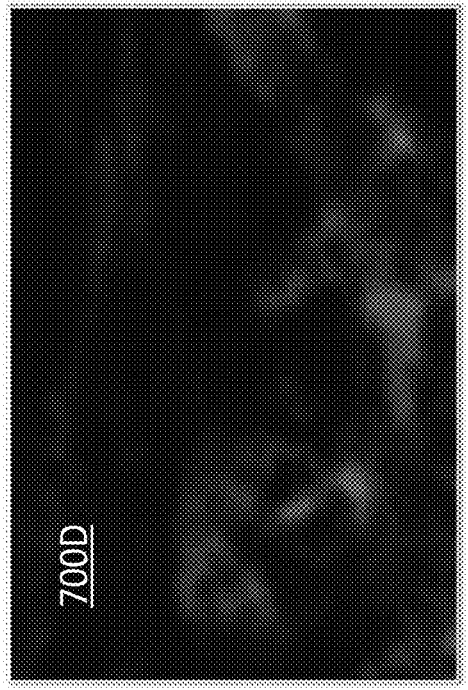

FIG. 7B illustrates image 700B, which is a cropped region of the GT image corresponding to images 600. Image 700B has a notably higher resolution (120*80 pixels) than image 700A.

Figure 7C:
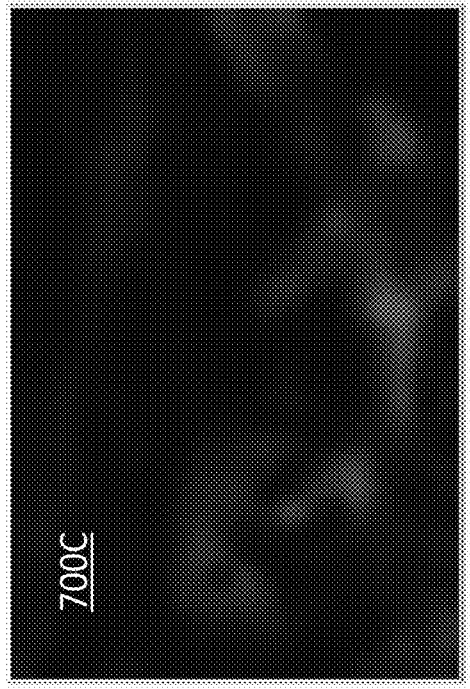

FIG. 7C illustrates image 700C, which is the same cropped region from HR image 600B, when the model used to obtain the HR is bicubic (resolution: 120*80 pixels).

Figure 7D:
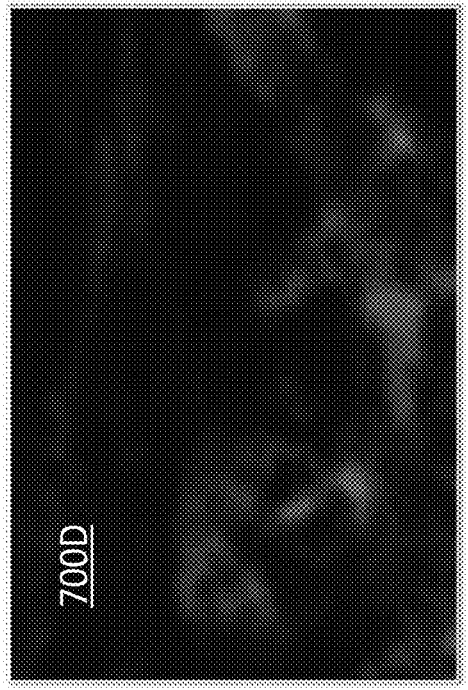

FIG. 7D illustrates image 700D, which is the same cropped region from HR image 600B, when the model used to obtain the HR is AI.

Figure 8B:
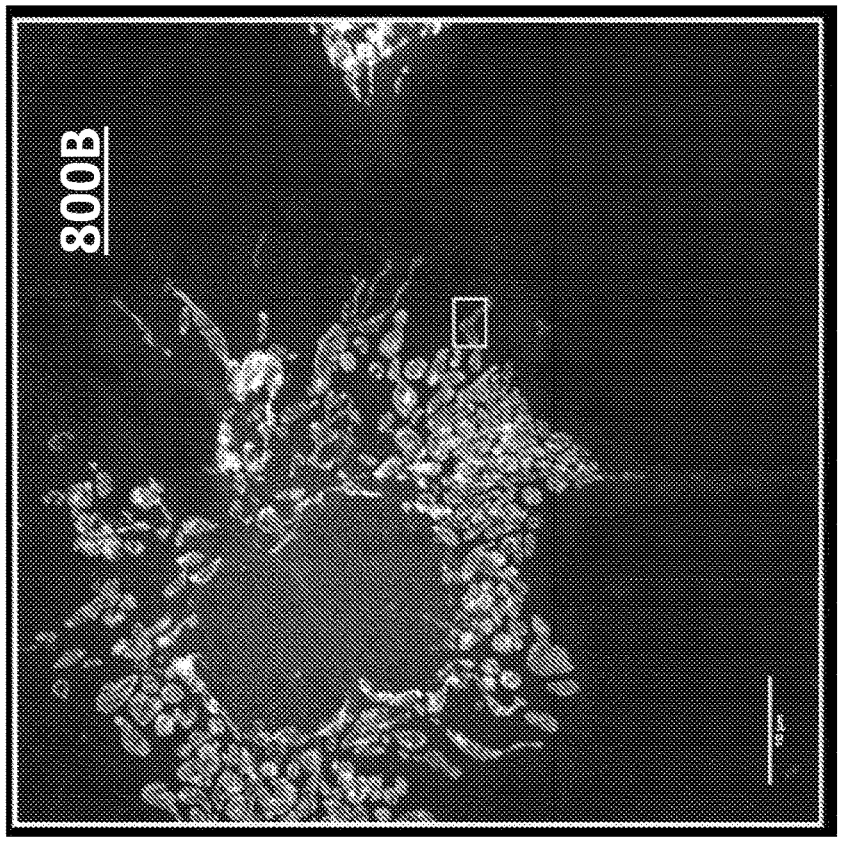
FIGS. 8A and 8B illustrate an image enhancement of a mitochondria obtained, according to various embodiments.
Figure 8A:

FIGS. 8A and 8B illustrate an image enhancement of a mitochondria obtained according to various embodiments (images 800A and 800B, hereinafter, collectively referred to as "images 800"). Images 800 may be collected using an imaging instrumentation communicatively coupled with a control device, as disclosed herein (e.g., control device 110 and imaging instrumentation 130, cf. FIGS. 1 and 2). The imaging instrumentation is a confocal microscope, and the sample is a mitochondrion. The image enhancement in images 800 may be obtained with an image processing engine and a model in the control device (e.g., image processing engine 222 and model 224, cf. FIG. 2).

FIG. 8A illustrates an LR grayscale image 800A (506*506 pixels) generated by a 4× manual down sampling of the GT image.

FIG. 8B illustrates an HR grayscale image 800B generated by the model in the image processing engine using an AI algorithm when LR 800A is given as the input (2024*2024 pixels).

FIGS. 9A through 9D illustrate an image enhancement of a portion of images 800, according to various embodiments (images 900A, 900B, 900C, and 900D, collectively referred to, hereinafter, as "images 900"). Images 900 show a detailed comparison of the same region cropped from images 800. The image enhancement in images 900 may be obtained with an image processing engine and a model in the control device (e.g., image processing engine 222 and model 224, cf. FIG. 2).

Figure 9A:
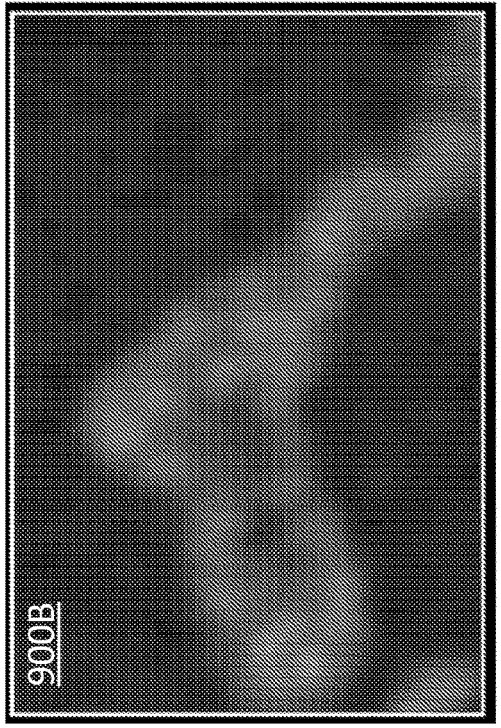
FIGS. 9A through 9D illustrate an image enhancement of a portion of the image in FIGS. 8A-8B obtained, according to various embodiments.

FIG. 9A illustrates image 900A, which is the region cropped directly from LR 800A (30*20 pixels).

Figure 9B:
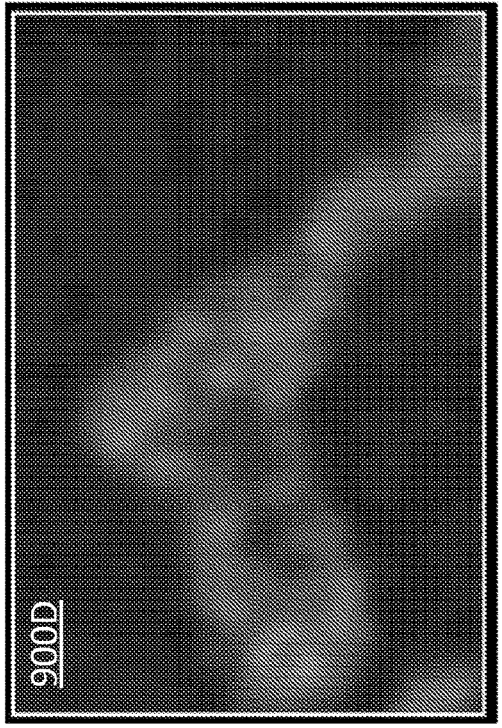

FIG. 9B illustrates image 900B, which is the same region cropped from the GT (120*80 pixels).

Figure 9C:
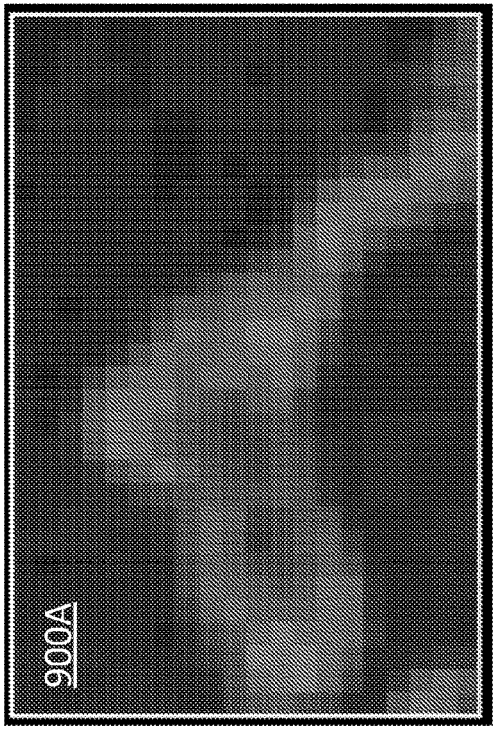

FIG. 9C illustrates image 900C, which is the same region cropped from HR 800B when the HR is generated by the model in the image processing engine using a bicubic algorithm (120*80 pixels).

Figure 9D:
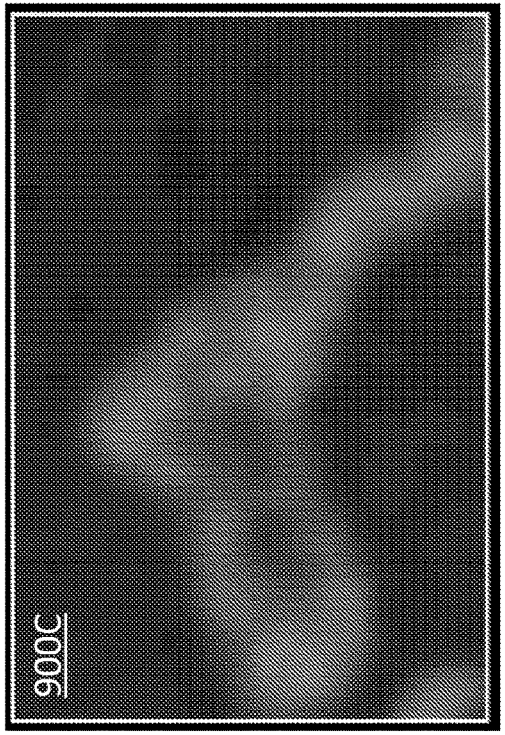

FIG. 9D illustrates image 900D, which is the same region cropped from HR 800B when the HR is generated by the model in the image processing engine using an AI algorithm (120*80 pixels).

Figures 10A, 10B, 10C:
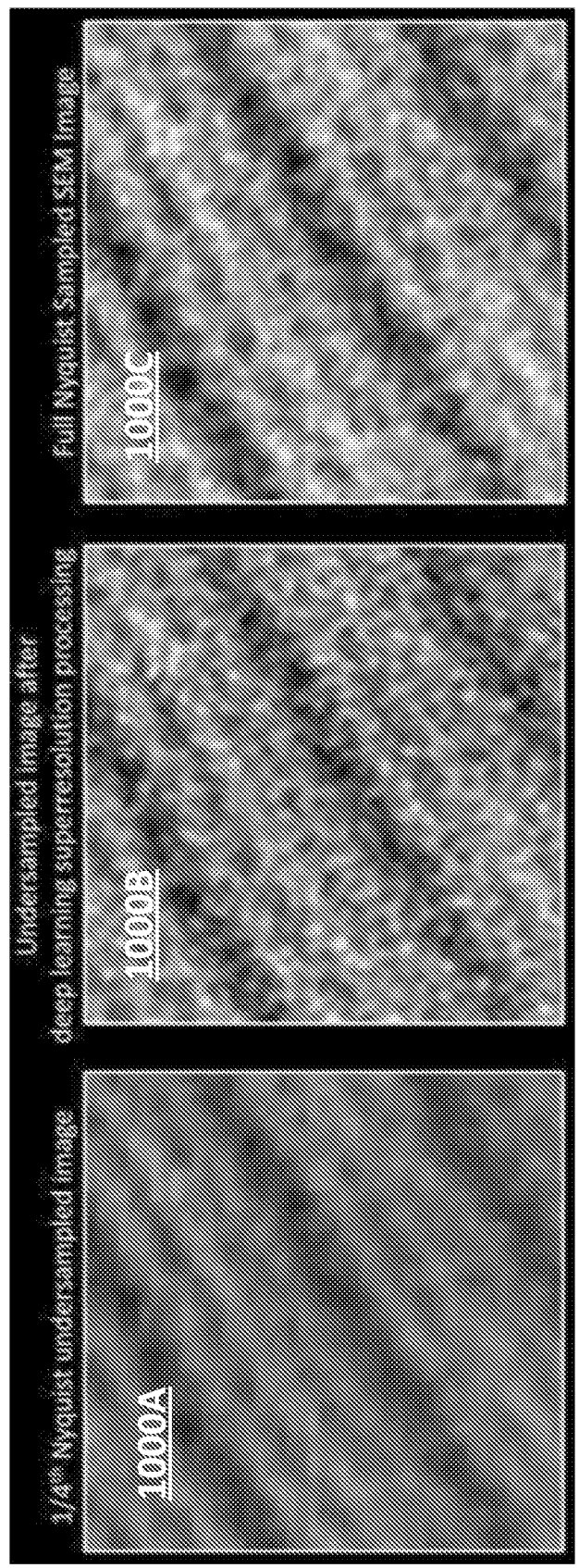
FIGS. 10A through 10C illustrate an image enhancement of a sub-Nyquist under sampled image obtained with a scanning electron microscope, according to various embodiments.

FIGS. 10A through 10C illustrate an image enhancement of a sub-Nyquist under sampled image obtained with a scanning electron microscope, according to various embodiments (images 1000A, 1000B, and 1000C, hereinafter, collectively referred to as "images 1000"). Images 1000 may be collected using an imaging instrumentation communicatively coupled with a control device, as disclosed herein (e.g., control device 110 and imaging instrumentation 130, cf. FIGS. 1 and 2). In some embodiments, the imaging instrumentation used to collect at least some of images 1000 is SEM. More specifically, images 1000 are related to a same 70 nm section of a myelin sheath in a neuronal network using SBFSEM instrumentation and techniques. Image enhancement in images 1000 may be obtained with an image processing engine and a model in the control device (e.g., image processing engine 222 and model 224, cf. FIG. 2). Images 1000A and 1000C were acquired using a pixel size of 8 nm on a backscatter detector at 1000 Volts (e.g., 1 kV) and a current of $221 \times 10^{-12}$ Amperes (e.g., 12 pico-A, or 12 pA). The pixel dwell time was $2 \times 10^{-6}$ seconds (e.g., 12 µs with an aperture of $30 \times 10^{-6}$ meters) (e.g., 30 micro-meters, or 30 µm) and a working distance of 6.81 millimeters (mm). The section thickness was $100 \times 10^{-9}$ meters (e.g., 100 nanometers nm) and the field of view was 24.5×24.5 µm.

FIG. 10A illustrates LR image 1000A, including a cropped region obtained with a 4× under sampled imaging instrumentation.

FIG. 10B illustrates HR image 1000B of the same cropped region as image 1000A, obtained with an AI model on LR image 1000A.

FIG. 10C illustrates GT image 1000C of the same cropped region as images 1000A and 1000B, obtained with a high-resolution imaging instrumentation. As can be seen, the quality of images 1000B and 1000C is comparable, the difference being that the collection of data for obtaining image 1000B (e.g., the scanning of image 1000A) is less invasive, less costly, and much faster than the collection of GT image 1000C.

Figure 11:
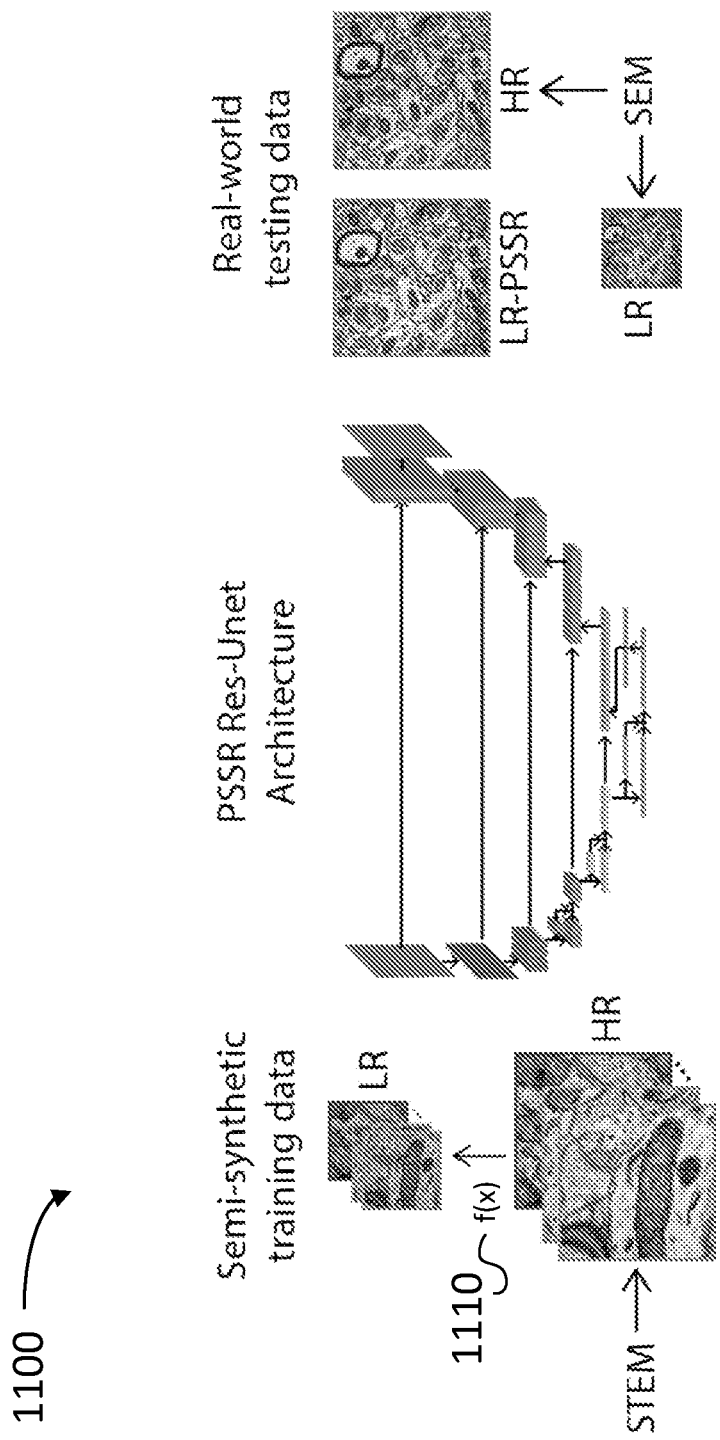
FIG. 11 illustrates a detailed block diagram for a semi-synthetic training scheme in a neural network for enhanced imaging, according to various embodiments.

FIG. 11 illustrates a detailed block diagram for a semi-synthetic training scheme 1100 (referred to, hereinafter, as "scheme 1100") in a neural network for enhanced imaging, according to various embodiments. Scheme 1100 may be applied to imaging instrumentation communicatively coupled with a control device via external links and a network, wherein the control device includes an image enhancement engine using a model (e.g., control device 110, external interfaces 218, image processing engine 222, model 224, network 150, and imaging instrumentation 130, cf. FIGS. 1 and 2). In some embodiments, semi-synthetic training scheme 1100 may be applied for training the model to be applied on specific applications, such as SBFSEM. More generally, semi-synthetic training schemes consistent with the present disclosure may be a semi-synthetic training scheme 1100 and applied to any other imaging instrumentation (e.g., imaging instrumentation 130, cf. FIG. 1). In some embodiments, it is desired to obtain a high resolution (e.g., 2 nm) and SNR necessary to reliably detect presynaptic vesicles. In some embodiments, the model may include a deep CNN (e.g., CNN 300 or CNN 400, cf. FIGS. 3 and 4) trained on 2 nm high-resolution (HR) images. Accordingly, in some embodiments, scheme 1100 may be used to train the model to "super-resolve" 8 nm low-resolution (LR) images to 2 nm resolution (PSSR model).

Scheme 1100 includes collecting a ~130 giga-byte (GB) dataset of 2 nm pixel STEM images of 40 nm ultrathin sections from the hippocampus of a male rat. The collection of the HR images may be performed over the network, using one of the external interfaces. To generate semi-synthetic training pairs, a down sampling scheme (e.g., 16× down sampling and the like) is applied to the HR images. In some embodiments, the LR image may be simply a manually acquired LR image (such as with a rapid scanning, low dosage point scan imaging instrumentation). In some embodiments, a semi-synthetic LR image obtained with down sampling schemes as disclosed herein may have a lower image quality than a manually acquired LR image. In some embodiments, scheme 1100 involves training a separate neural network to generate LR images. Alternatively, Gaussian and/or Poisson noise and blur may be added to the images in addition to pixel downsampling to generate LR images. Each of the HR images is paired with its corresponding LR image obtained from the down sampling scheme to form an HR-LR image pair. Scheme 1300 then trains the HR-LR image pairs on a ResNet-based U-Net model (e.g., CNN as disclosed herein, cf. FIGS. 3 and 4). In some embodiments, scheme 1300 may include a mean squared error (MSE) loss function that may produce visually improved results, with high Peak SNR (PSNR) and positive Structural Similarity (SSIM) measurements.

Scheme 1100 includes evaluation metrics to determine image quality. A first metric may include a PSNR metric. In some embodiments, scheme 1100 also uses an SSIM metric. PSNR and SSIM provide pixel-level data fidelity and perceptual quality fidelity correspondingly. The specific selection of a quality metric to use in scheme 1100 is non-limiting of embodiments consistent with the present disclosure. PSNR is negatively correlated with MSE, numerically reflecting the pixel intensity difference between the reconstruction image and the ground truth image, but it is also famous for poor performance when it comes to estimating human perceptual quality. Instead of traditional error summation methods, SSIM is designed to consider distortion factors like Luminance distortion, contrast distortion, and loss of correlation when interpreting image quality.

Scheme 1100 incudes collecting real-world LR images with the same pixel dwell time as the HR data, resulting in 16× lower signal for the real-world LR images (e.g., because there are 16× fewer pixels). In some embodiments, HR-STEM training images may have a higher image quality than the HR validation dataset acquired on an SEM (e.g., for obtaining the CNN model that is to be trained with scheme 1100). Accordingly, in some embodiments, scheme 1300 may produce a model that is trained to restore an LR collected image into an HR synthetic image having a higher image quality than an HR collected image using the same imaging instrumentation. Moreover, scheme 1100 also provides a model that may be used with a wider range of real world data, including data extracted from a database, through the network, and which was collected from a different imaging instrumentation at a different location, through the network.

Low-resolution (LR) images were generated from high-resolution (HR) EM or confocal images using an image baselining function 1110. Due to the variance of image format, image size, dynamic range, depth, and the like in the acquired high-resolution images, data cleaning is desirable to generate training sets that can be easily accessed during training. Consistent with this disclosure, "data sources" may refer to uncleaned images acquired with high-resolution imaging instrumentation, while "data sets" may refer to images generated and preprocessed from "data sources." In addition to baselining function 1110, some embodiments include a data augmentation tool such as random cropping, dihedral affine function, rotation, and random zoom to increase the variety and size of the training data.

Figure 12A:
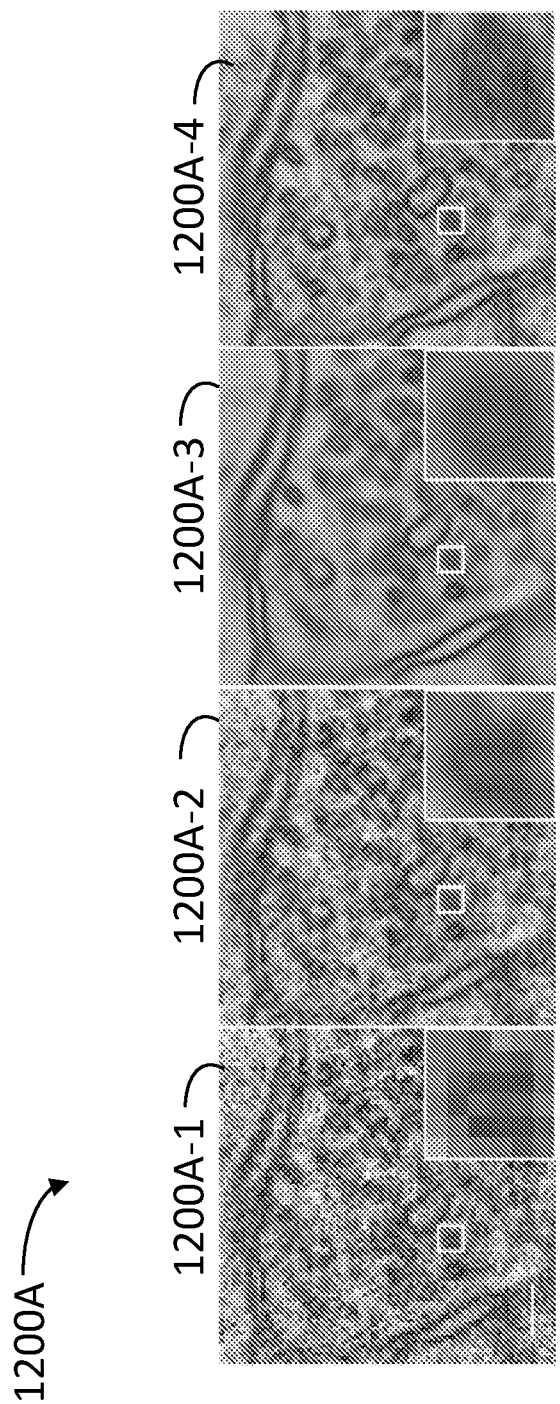
FIGS. 12A through 12C illustrate some applications of the neural network in FIG. 11 for electron microscopy, according to various embodiments.
Figure 12B:
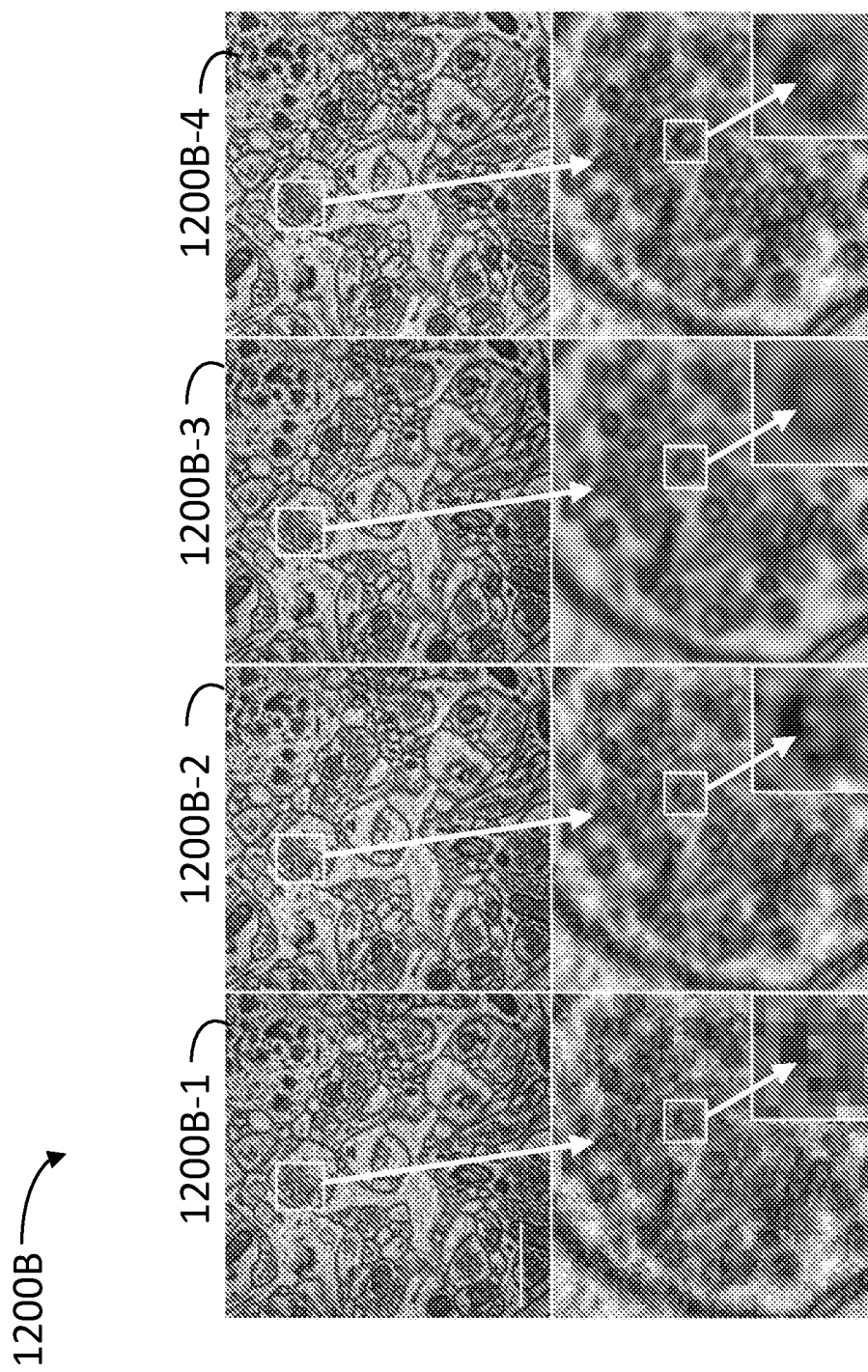
Figure 12C:
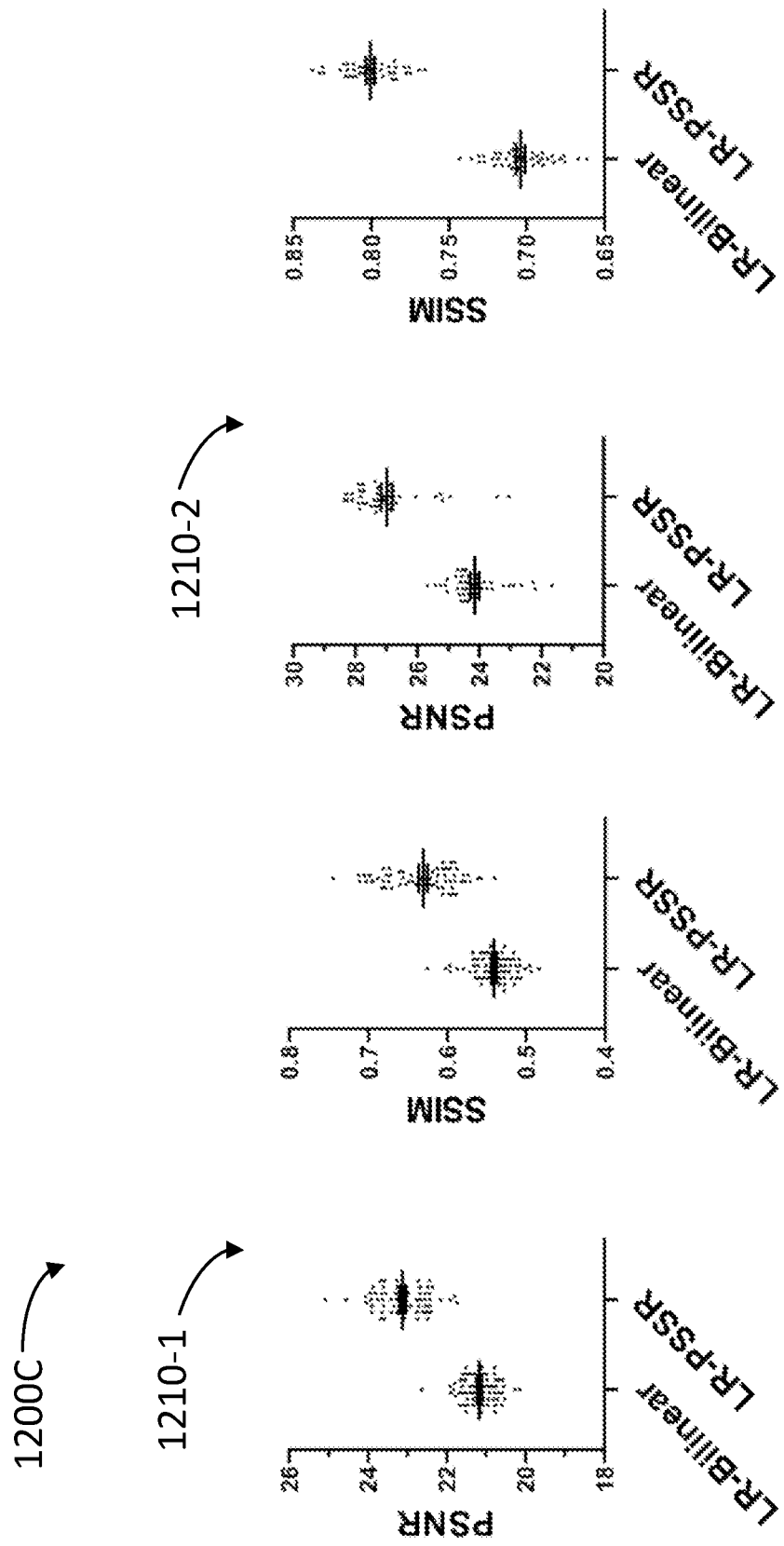

FIGS. 12A through 12C illustrate some applications of a neural network for electron microscopy, according to various embodiments (images 1200A and 1200B, collectively referred to, hereinafter, as "images 1200"). Some of images 1200 may be collected using an imaging instrumentation communicatively coupled with a control device, as disclosed herein (e.g., control device 110 and imaging instrumentation 130, cf. FIGS. 1 and 2). Some of images 1200 may be obtained through a model in an image processing engine, as disclosed herein (e.g., image processing engine 222 and model 224, cf. FIG. 2). In some embodiments, the model may be further trained with a semi-synthetic training scheme, as disclosed herein (e.g., scheme 1100, cf. FIG. 11). Images 1200 may be obtained by the controller device via external links and a network (e.g., external interfaces 218 and network 150, cf. FIGS. 1 and 2). Images 1200 correspond to STEM images of 40 nm ultrathin sections from the hippocampus of a male rat. In some embodiments and without limitation, some of the images may correspond to 80 nm sections imaged with a backscatter detector. Without limiting the scope of embodiments disclosed herein, and for illustrative purposes only, the HR in images 1200 corresponds to a 2 nm resolution, and in some embodiments, the LR corresponds to an 8 nm resolution.

FIG. 12A illustrates images 1200A including LR image 1200A-1, a synthetic HR image 1200A-2 (wherein the up sampling algorithm includes a bilinear interpolation), a synthetic HR image 1200A-3 (wherein the up sampling algorithm includes a PSSR model), and a collected HR image 1200A-4 (e.g., imaging instrumentation operating in high-resolution mode, or GT image). The PSSR-restored images from the semi-synthetic pairs contained more detail and yet displayed less noise, making it easier to discern fine details such as presynaptic vesicles.

FIG. 12B illustrates images 1200B including LR image 1200B-1, a synthetic HR image 1200B-2 (wherein the up sampling algorithm includes a bilinear interpolation), a synthetic HR image 1200B-3 (wherein the up sampling algorithm includes a PSSR model), and a collected HR image 1200B-4 (e.g., imaging instrumentation operating in high-resolution mode, or GT image). The PSSR-restored images from the semi-synthetic pairs contained more detail and yet displayed less noise, making it easier to discern fine details such as presynaptic vesicles. The second row of images 1200B is the zoomed in image corresponding to the cropped region, as indicated in the first row of FIG. 1200B. A further zoom in view of a crop region is indicated in the inset for images 1200B in the second row.

FIG. 12C illustrates charts 1200C with tests of the image quality obtained after enhancing LR images with either a bilinear interpolation model and a PSSR model for both STEM instrumentation (graphs 1210-1) and SEM instrumentation (graphs 1210-2). Graphs 1210-1 and 1210-2 will be collectively referred to, hereinafter, as "graphs 1210." Each data point in graphs 1210 is associated to an image pair, indicating at least one LR image collection and one HR image collection (to use as a GT point of comparison). Thus, in some embodiments, the multiple images used to form graphs 1210 may be retrieved from multiple instruments in multiple remote locations, through the network. Graphs 1210 include two different image quality metrics: PSNR and SSIM, which illustrate the robustness of deep learning-based image restoration models as disclosed herein with respect to variations in image properties, notwithstanding the use of a model generated from training images acquired in one condition on images acquired in another (e.g., data generated using a different sample preparation technique, type, or on a different microscope). PSSR significantly increases both the resolution and quality (PSNR, SSIM) of manually acquired low-resolution images. Thus, PSSR models as disclosed herein may be applied to data acquired by different instruments, and even with different techniques and samples.

Mouse FIB-SEM data sample preparation and image acquisition settings were previously described in the original manuscript the datasets were published. Briefly, the images were acquired with 4 nm voxel resolution. We down sampled the lateral resolution to 8 nm, and then applied the PSSR model to the down sampled data to ensure the proper 8-to-2 nm transformation for which the PSSR was trained.

The rat SEM data sample was acquired from an 8-week old male Wistar rat that was anesthetized with an overdose of pentobarbital (75 mg kg-1) and perfused through the heart with 5-10 ml of a solution of 250 mM sucrose 5 mM $MgCl_2$ in 0.02 M phosphate buffer (pH 7.4) (PB) followed by 200 ml of 4% paraformaldehyde containing 0.2% picric acid and 1% glutaraldehyde in 0.1 M PB. Brains were then removed and oblique horizontal sections (50 μm thick) of frontal cortex/striatum were cut on a vibrating microtome along the line of the rhinal fissure. The tissue was stained and cut to 50 nm sections using ATUMtome for SEM imaging. The rat SEM data was acquired using an acceleration voltage of 1.5 kV and a dwell time of 3 μs, using the backscatter detector with a pixel resolution of 10×10 nm (which was up sampled to 8 nm using bilinear interpolation).

FIGS. 13A through 13E illustrate some applications of a neural network for electron microscopy, according to various embodiments. Images 1300A, 1300B, 1300C, 1300D, and 1300E (hereinafter, collectively referred to as "images 1300") may be collected using an imaging instrumentation communicatively coupled with a control device, as disclosed herein (e.g., control device 110 and imaging instrumentation 130, cf. FIGS. 1 and 2). Some of images 1300 may be obtained through a model in an image processing engine, as disclosed herein (e.g., image processing engine 222 and model 224, cf. FIG. 2). In some embodiments, the model may be further trained with a semi-synthetic training scheme, as disclosed herein (e.g., scheme 1300, cf. FIG. 13). Images 1300 may be obtained by the controller device via external links and a network (e.g., external interfaces 218 and network 150, cf. FIGS. 1 and 2). Images 1300 correspond to brain tissue (neuronal networks and synaptic interfaces). In some embodiments and without limitation, some of the images may correspond to mouse, rat, and fly samples imaged on four different microscopes in four different data sources (e.g., laboratories). Without limiting the scope of embodiments disclosed herein, and for illustrative purposes only, the HR in images 1300 corresponds to a 2 nm resolution, and in some embodiments, the LR corresponds to an 8 nm resolution.

In some embodiments (e.g., fly brain tissue), at least some of images 1300 include FIB-SEM imaging instrumentation. For this, images may be acquired with 10 nm voxel resolution and up sampled to 8 nm using bilinear interpolation. A PSSR model is applied to the up sampled data to obtain an 8 nm-to-2 nm transformation (for which the PSSR model was trained). In addition to the SBFSEM and FE-SEM imaging systems, PSSR processing appeared to restore images 1300 from multiple data sources. In some embodiments, a further segmentation step using a segmentation tool (e.g., segmentation tool 226, cf. FIG. 2) after applying image enhancement with the PSSR model is substantially simplified, and can be performed automatically, without human intervention, according to some embodiments. A segmentation step is desirable for analyzing 3DEM datasets. Remarkably, the PSSR model also performed well on a 10×10×10 nm resolution FIB-SEM fly brain dataset, resulting in a 2×2×10 nm resolution dataset with higher SNR and resolution. Thus, a PSSR model as disclosed herein may be used for a down sampling factor of 25×, or even higher, increasing the lateral resolution and speed of FIB-SEM imaging by a factor of up to 25×, or maybe more.

Figure 13A:
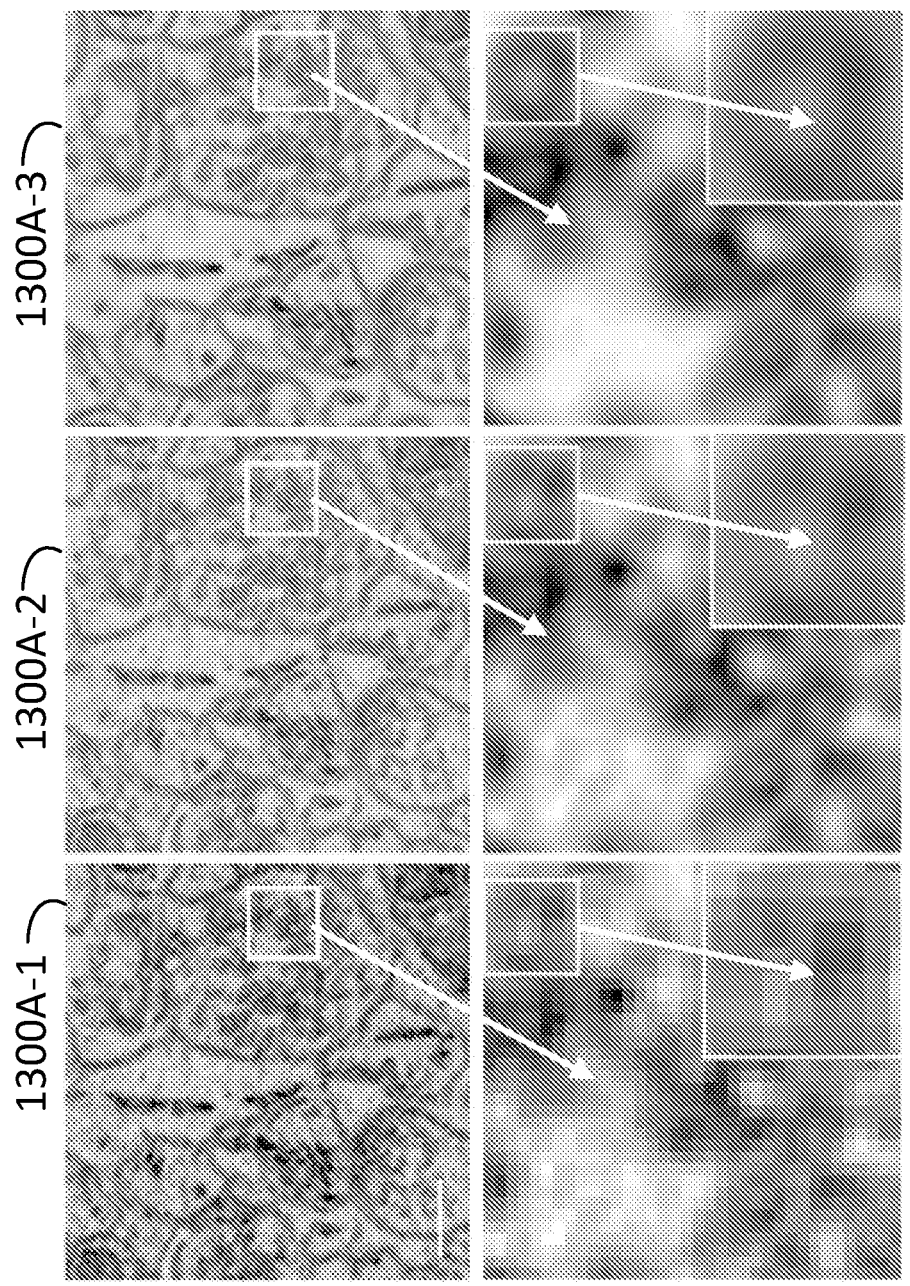
FIGS. 13A through 13E illustrate some applications of the neural network in FIG. 11 for electron microscopy, according to various embodiments.

FIG. 13A illustrates images 1300A from a portion of a mouse brain tissue. Images 1300A include LR image 1300A-1, a synthetic HR image 1300A-2 (wherein the up sampling algorithm includes a bilinear interpolation), and a synthetic HR image 1300A-3 (wherein the up sampling algorithm includes a PSSR model). The PSSR-restored images from the semi-synthetic pairs contained more detail and yet displayed less noise, making it easier to discern fine details such as presynaptic vesicles. The second row of images 1300A is the zoomed in image corresponding to the cropped region, as indicated in the first row of FIG. 1300A. A further zoom in view of a crop region is indicated in the inset for images 1300A in the second row. Images 1300A show that the PSSR model is able to restore an 8 nm pixel SBFSEM 3D dataset to 2 nm.

Figure 13B:
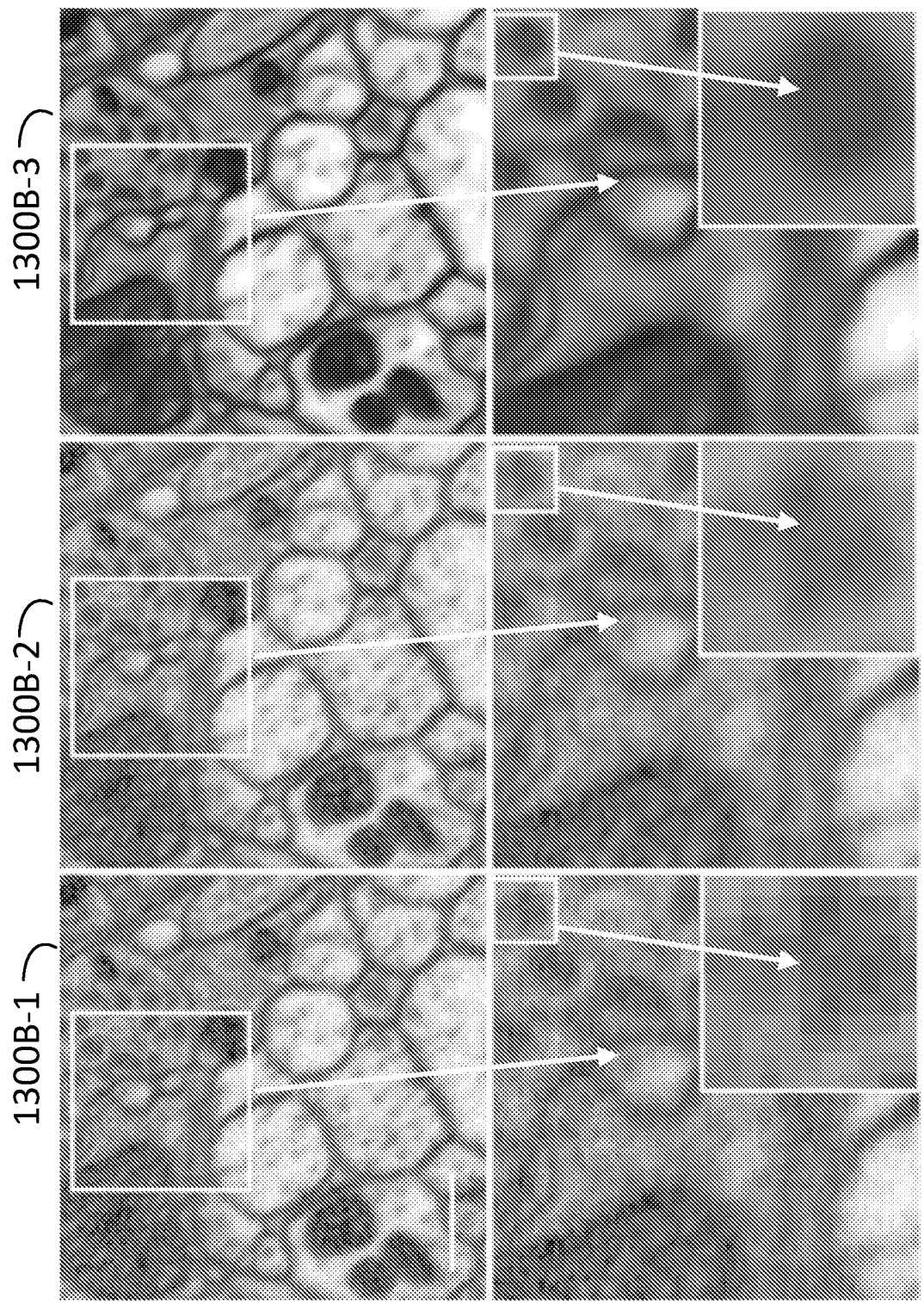

FIG. 13B illustrates images 1300B from a portion of a fly brain tissue. Images 1300B include LR image 1300B-1, a synthetic HR image 1300B-2 (wherein the up sampling algorithm includes a bilinear interpolation), and a synthetic HR image 1300B-3 (wherein the up sampling algorithm includes a PSSR model). The PSSR-restored images from the semi-synthetic pairs contained more detail and yet displayed less noise, making it easier to discern fine details such as presynaptic vesicles. The second row of images 1300B is the zoomed in image corresponding to the cropped region, as indicated in the first row of FIG. 1300B. A further zoom in view of a crop region is indicated in the inset for images 1300B in the second row.

Figure 13C:
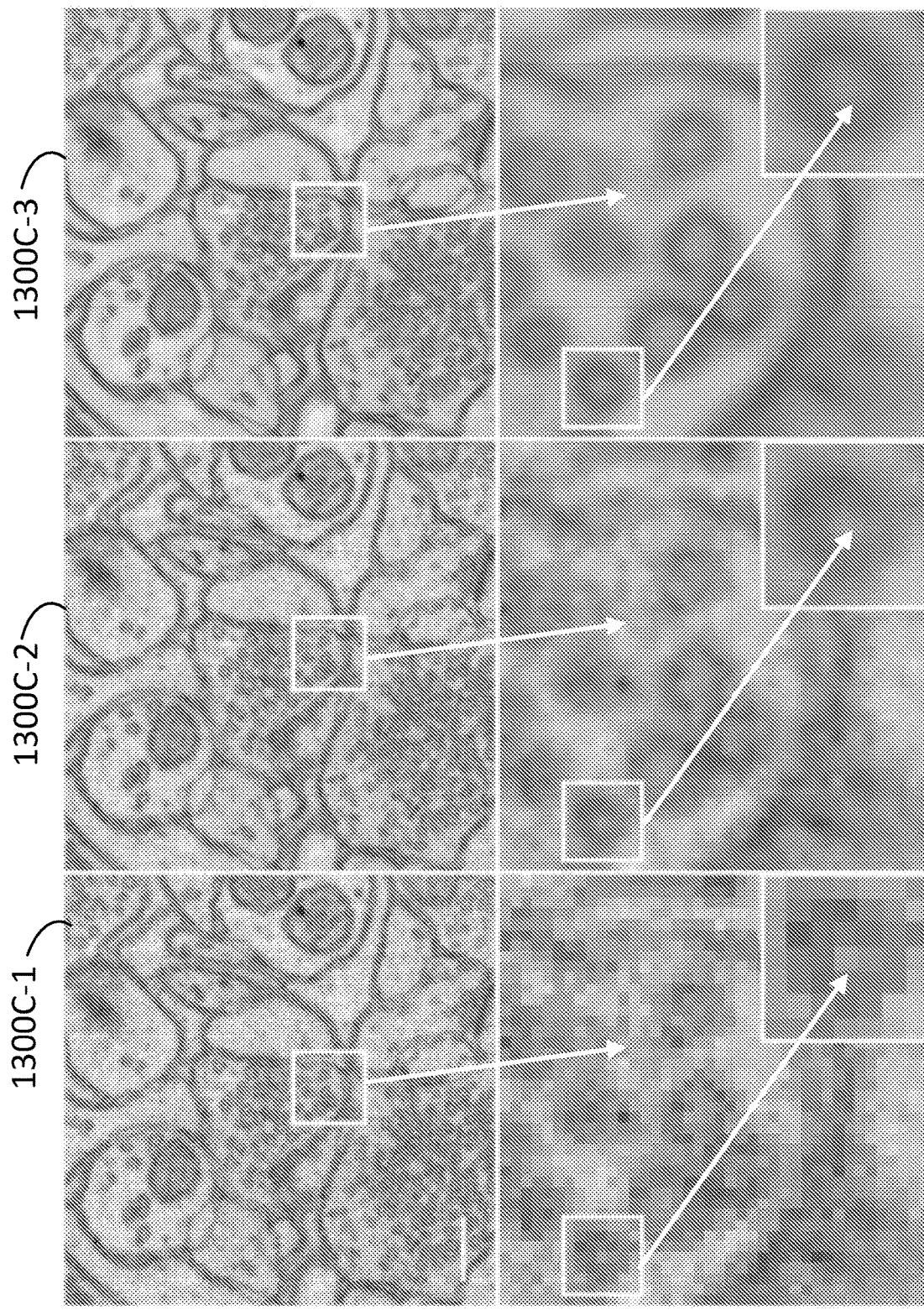

FIG. 13C illustrates images 1300C from a mouse brain tissue. Images 1300C include LR image 1300C-1, a synthetic HR image 1300C-2 (wherein the up sampling algorithm includes a bilinear interpolation), and a synthetic HR image 1300C-3 (wherein the up sampling algorithm includes a PSSR model). The PSSR-restored images from the semi-synthetic pairs contained more detail and yet displayed less noise, making it easier to discern fine details such as presynaptic vesicles. The second row of images 1300C is the zoomed in image corresponding to the cropped region, as indicated in the first row of FIG. 1300C. A further zoom in view of a crop region is indicated in the inset for images 1300C in the second row.

Figure 13D:
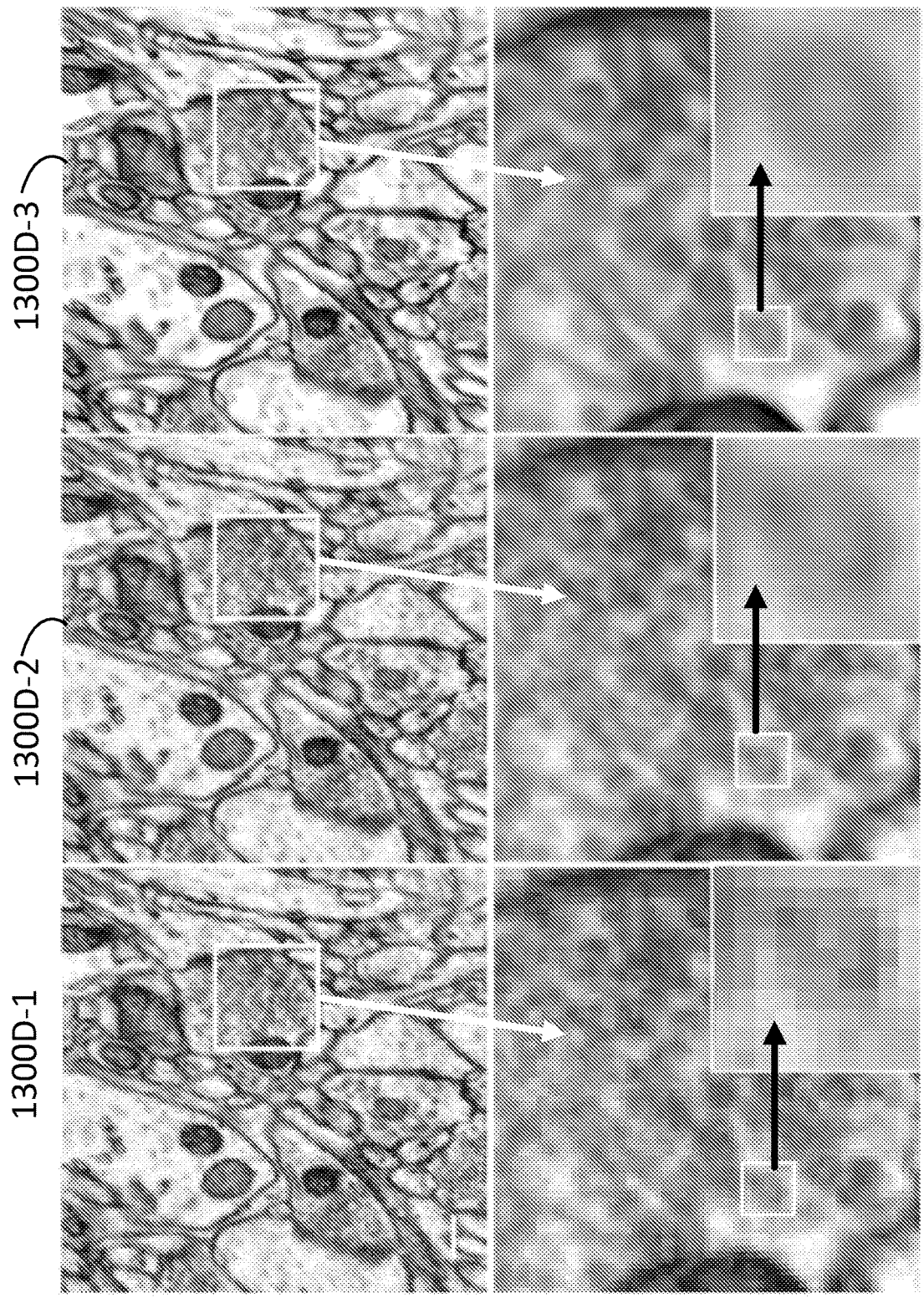

FIG. 13D illustrates images 1300D from a rat brain tissue. Images 1300D include LR image 1300D-1, a synthetic HR image 1300D-2 (wherein the up sampling algorithm includes a bilinear interpolation), and a synthetic HR image 1300D-3 (wherein the up sampling algorithm includes a PSSR model). The PSSR-restored images from the semi-synthetic pairs contained more detail and yet displayed less noise, making it easier to discern fine details such as presynaptic vesicles. The second row of images 1300D is the zoomed in image corresponding to the cropped region, as indicated in the first row of FIG. 1300D. A further zoom in view of a crop region is indicated in the inset for images 1300D in the second row.

Figure 13E:
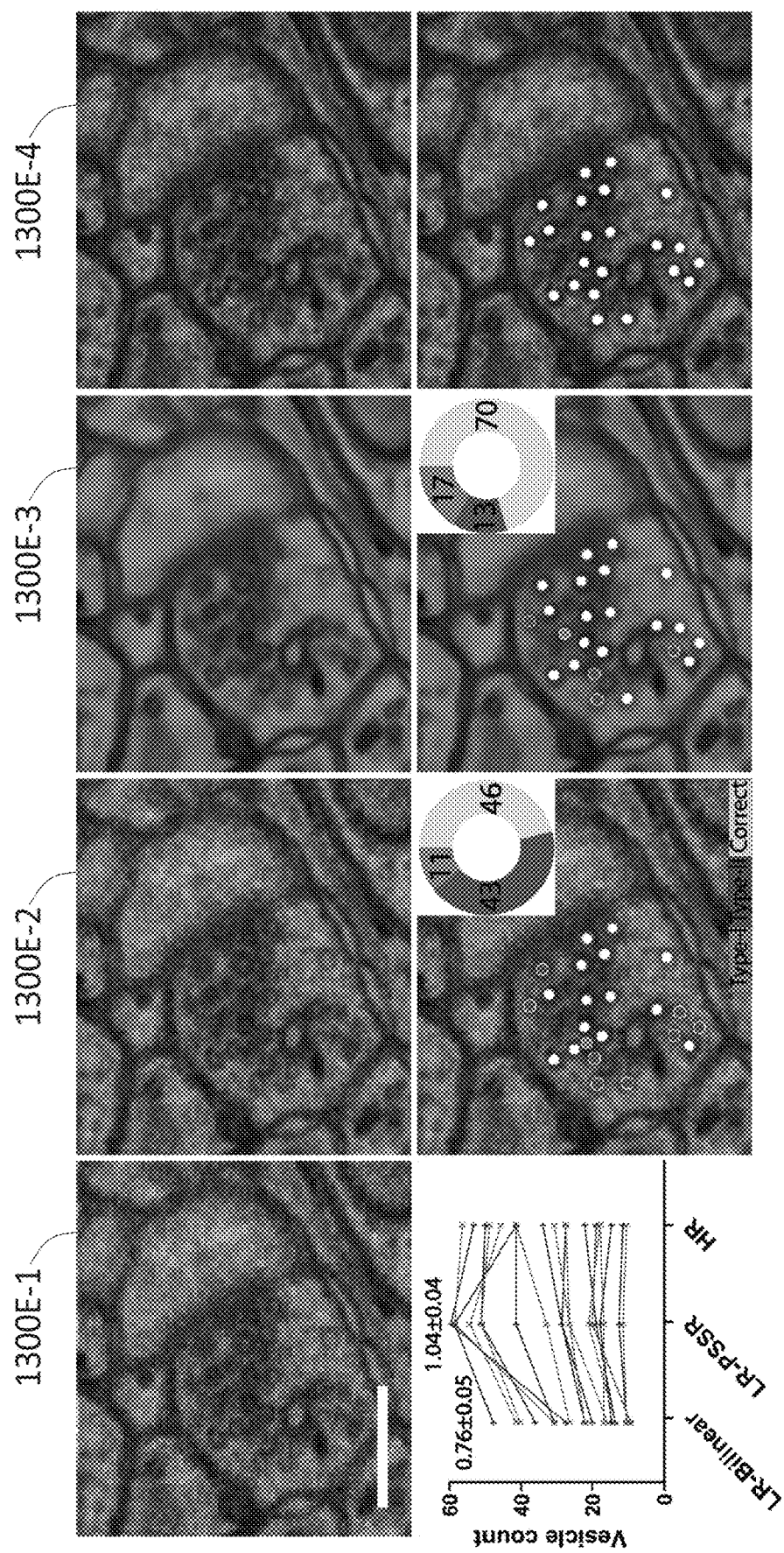
Figure 13E:
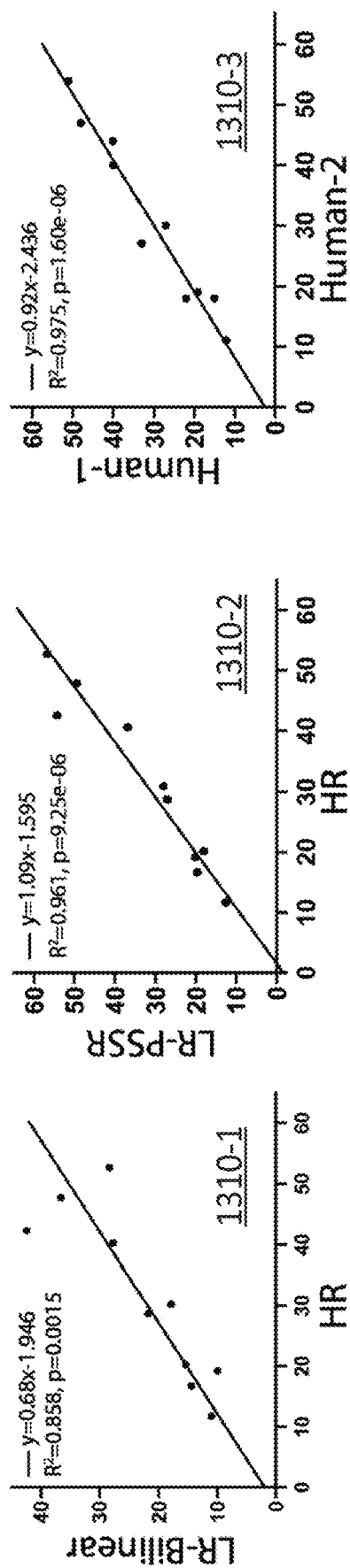

FIG. 13E illustrates images 1300E-1, 1300E-2, 1300E-3, and 1300E-4 (hereinafter, collectively referred to as "images 1300E") from a rat brain tissue. Images 1300E include LR image 1300E-1, a synthetic HR image 1300E-2 (wherein the up sampling algorithm includes a bilinear interpolation), a synthetic HR image 1300E-3 (wherein the up sampling algorithm includes a PSSR model), and a collected HR image 1300E-4 (e.g., imaging instrumentation operating in high-resolution mode, or GT image). The PSSR-restored images from the semi-synthetic pairs contained more detail and yet displayed less noise, making it easier to discern fine details such as presynaptic vesicles.

Graphs 1310-1, 1310-2, and 1310-3 (hereinafter, collectively referred to as "graphs 1310") indicate an image processing accuracy, with emphasis on the possibility of false positives (e.g., artifacts or "hallucinations"). Some of images 1300E (e.g., HR synthetic images 1300E-3) include 2 nm pixel SBFSEM datasets which may be beyond the capabilities for at least some imaging instrumentation used. In some embodiments, this may preclude the generation of GT validation images for the SBFSEM data (e.g., GT images 1300E-4). To identify a trust level of processed datasets for which no GT data exists, some embodiments include determining whether the PSSR model is sufficiently accurate for useful downstream analysis.

To do this, at least some of images 1300E include low 8 nm and high 2 nm pixel resolution SEM image pairs of ultrathin sections. Further, some images 1300E include 16× super-sampled of the 8 nm pixel images (LR) to 2 nm pixel images (HR) using either bilinear interpolation or a PSSR model. The image quality (PSNR and/or SSIM) of LR-bilinear and LR-PSSR models for the above two procedures should be equal in the absence of artifacts (slope=1 in graphs 1310). Comparing the image quality of the resulting HR synthetic images 1300E-4 for the two cases, it is seen that LR-PSSR (cf. graph 1310-2) significantly outperforms LR-bilinear (cf. graph 1310-1). To further test the accuracy and utility of the PSSR output in a more concrete, biological context, graph 1310-3 illustrates a randomized LR-bilinear, LR-PSSR, and HR images, wherein two blinded human experts perform manual segmentation of presynaptic vesicles (one human for each of the two up sampling procedures). Graphs 1310 illustrate that LR-PSSR is significantly more accurate than the LR-bilinear, and even the two human experts. In some embodiments, the LR-PSSR output reduced false negatives by ~300%, and the LR-PSSR output may have a slightly higher number of "false positives" than the LR-bilinear. However, since the HR data is noisier than both the training data as well as the LR-PSSR output, it is possible that not all of the false positives are truly false. Moreover, the variance between the LR-PSSR and HR results was similar to the variance between the two expert human results on HR data. The human results in fact may be a gold standard (near maximum accuracy and precision possible). Graphs 1310 reveal that in some embodiments, PSSR models as disclosed herein may effectively produce 2 nm 3DEM data from 8 nm resolution acquisitions, revealing important subcellular structures, otherwise lost in many 3DEM datasets. Furthermore, the ability to reliably 16× super-sample lower resolution datasets presents an opportunity to increase the throughput of SEM imaging by at least one order of magnitude, according to some embodiments.

FIGS. 14A through 14K illustrate some applications in confocal fluorescence microscopy, according to various embodiments. Images 1400A, 1400B, 1400C, 1400D, 1400E, and 1400F (hereinafter, collectively referred to as "images 1400") may be collected using an imaging instrumentation communicatively coupled with a control device, as disclosed herein (e.g., control device 110 and imaging instrumentation 130, cf. FIGS. 1 and 2). The imaging instrumentation used may include a laser scanning confocal microscope. Some of images 1400 may be obtained through a model in an image processing engine, as disclosed herein (e.g., image processing engine 222 and model 224, cf. FIG. 2). In some embodiments, the model may be further trained with a semi-synthetic training scheme, as disclosed herein. Images 1400 may be obtained by the controller device via external links and a network (e.g., external links 218 and network 150, cf. FIGS. 1 and 2). For example, in some embodiments, a ~5 GB of high-resolution confocal time lapses of mitochondrial transport in neurons may be either collected or downloaded from the network. Images 1400 show that a PSSR model as disclosed herein may up sample and restore under sampled confocal images obtained with standard imaging instrumentation (e.g., using a single photomultiplier tube—PMT—detector), to an HR image having an image quality comparable to the GT (e.g., gold standard in imaging instrumentation). Using the fine-tuned PSSR model, images 1400 include restored HR images from down to 16× lower resolution. Accordingly, in some embodiments, scheme 1600 may provide a PSSR model enabling 16× faster time lapses of neuronal mitochondria motility to sufficient resolution for proper analysis. Without limiting the scope of embodiments disclosed herein, and for illustrative purposes only, some of the HR images 1400 and the LR images 1400 have similar resolution of laser scanning confocal images as disclosed herein.

Figure 14A:
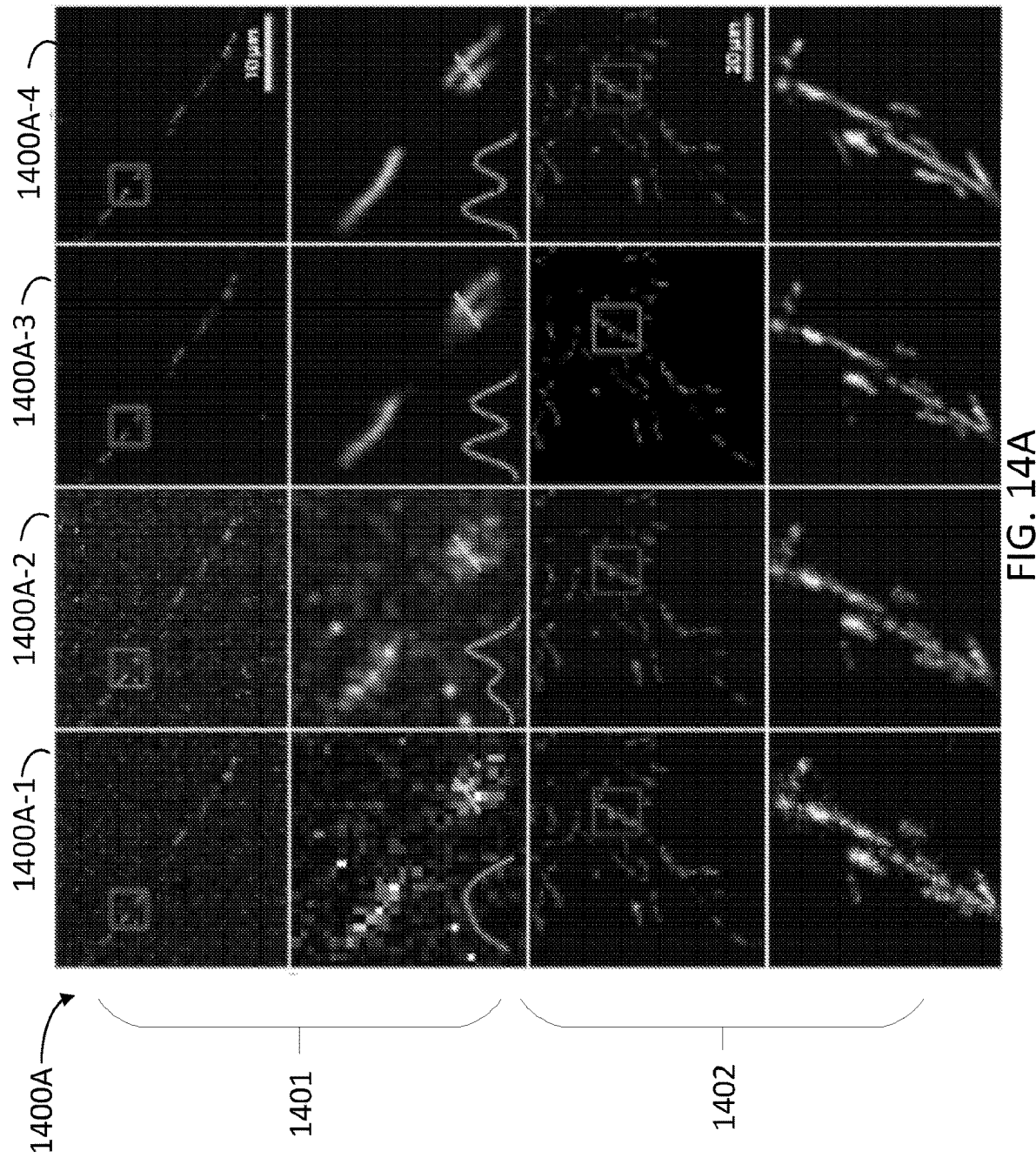

FIG. 14A illustrates images 1400A including LR image 1400A-1, a synthetic HR image 1400A-2 (wherein the up sampling algorithm includes a bilinear interpolation), a synthetic HR image 1400A-3 (wherein the up sampling algorithm includes a PSSR model), and a collected HR image 1400A-4 (e.g., imaging instrumentation operating in high-resolution mode, or GT image). Moreover, images 1400A may be split into semi-synthetic rows 1401 (downloaded images from the network, or synthetically down sampled HR images), and real-world rows 1402 (images collected with imaging instrumentation).

Figure 14B:
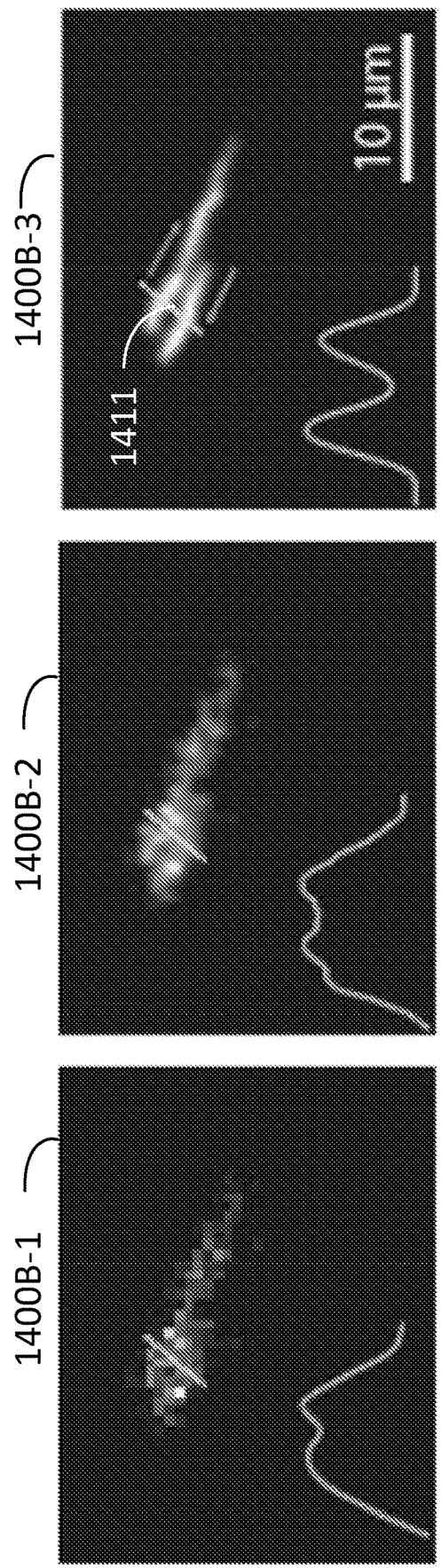

FIG. 14B illustrates images 1400B including LR image 1400B-1, a synthetic HR image 1400B-2 (wherein the up sampling algorithm includes a bilinear interpolation), and a synthetic HR image 1400B-3 (wherein the up sampling algorithm includes a PSSR model). The improved speed, resolution, and SNR observed in image 1400B-3 enables detection of mitochondrial traffic event 1411 that were not detectable in LR image 1400B-1.

Figure 14C:
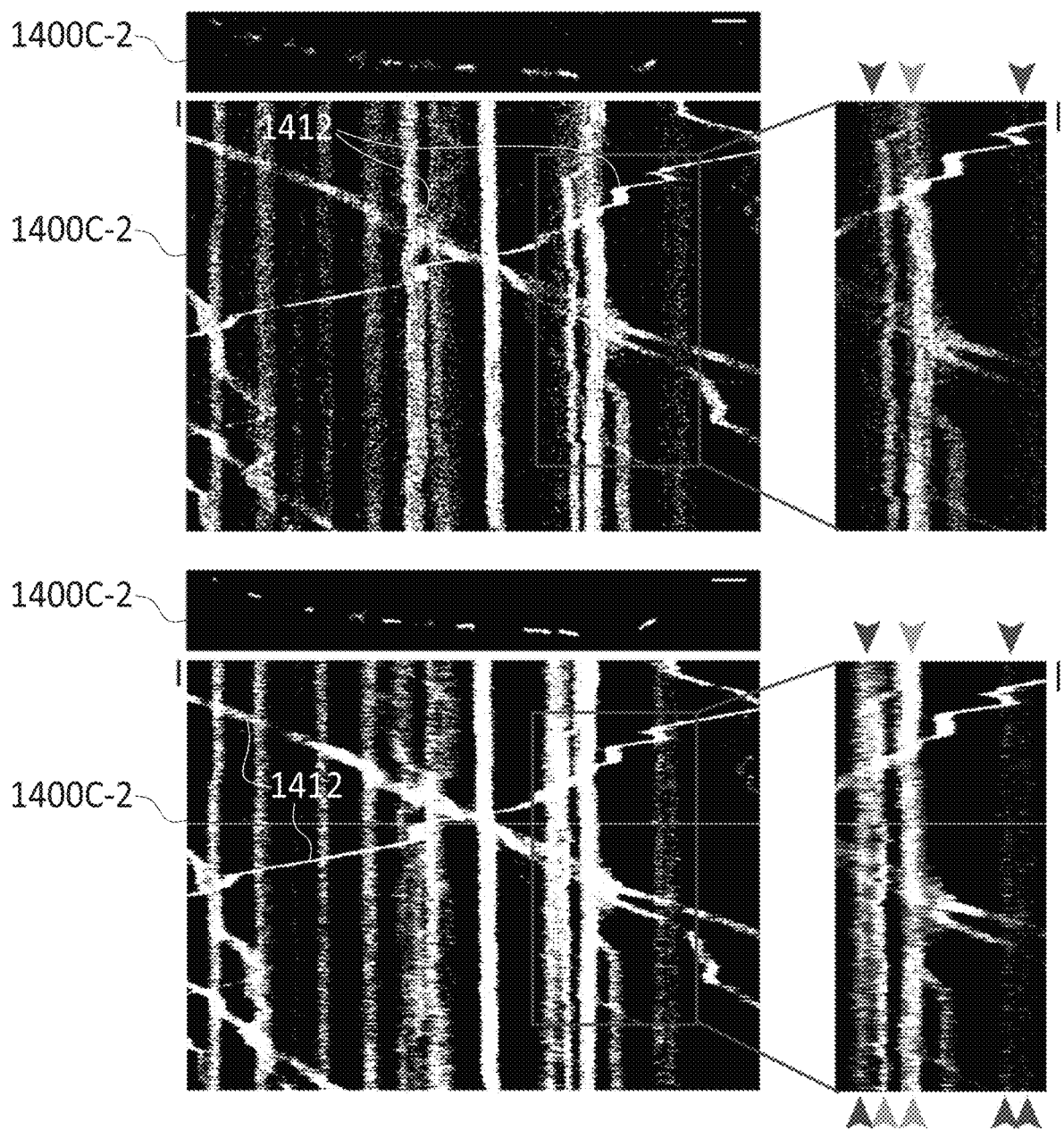

FIG. 14C illustrates images 1400C including LR image 1400C-1, and a synthetic HR image 1400C-2 (wherein the up sampling algorithm includes a PSSR model). Images 1400C illustrate a number of mitochondria within a neuronal cytoplasm. Images 1401-1 and 1401-2 (collectively referred to, hereinafter, as "streak images 1401") illustrate a time-lapse (with time proceeding downward) streak of the two-dimensional images 1400C, respectively (1801-1 for the LR-confocal collection, and 1401-2 for the synthetic HR up sampling image using the PSSR model). A zoomed-in portion illustrates some detail in streak images 1401. Traces 1412 in streak images 1401 indicate a moving mitochondrion, and the slope of traces 1412 indicates the speed. Clearly, the SNR in image 1400C-2 and streak image 1401-2 is substantially higher than in the corresponding LR source (e.g., image 1400C-1 and streak image 1401-1).

Figure 14D:
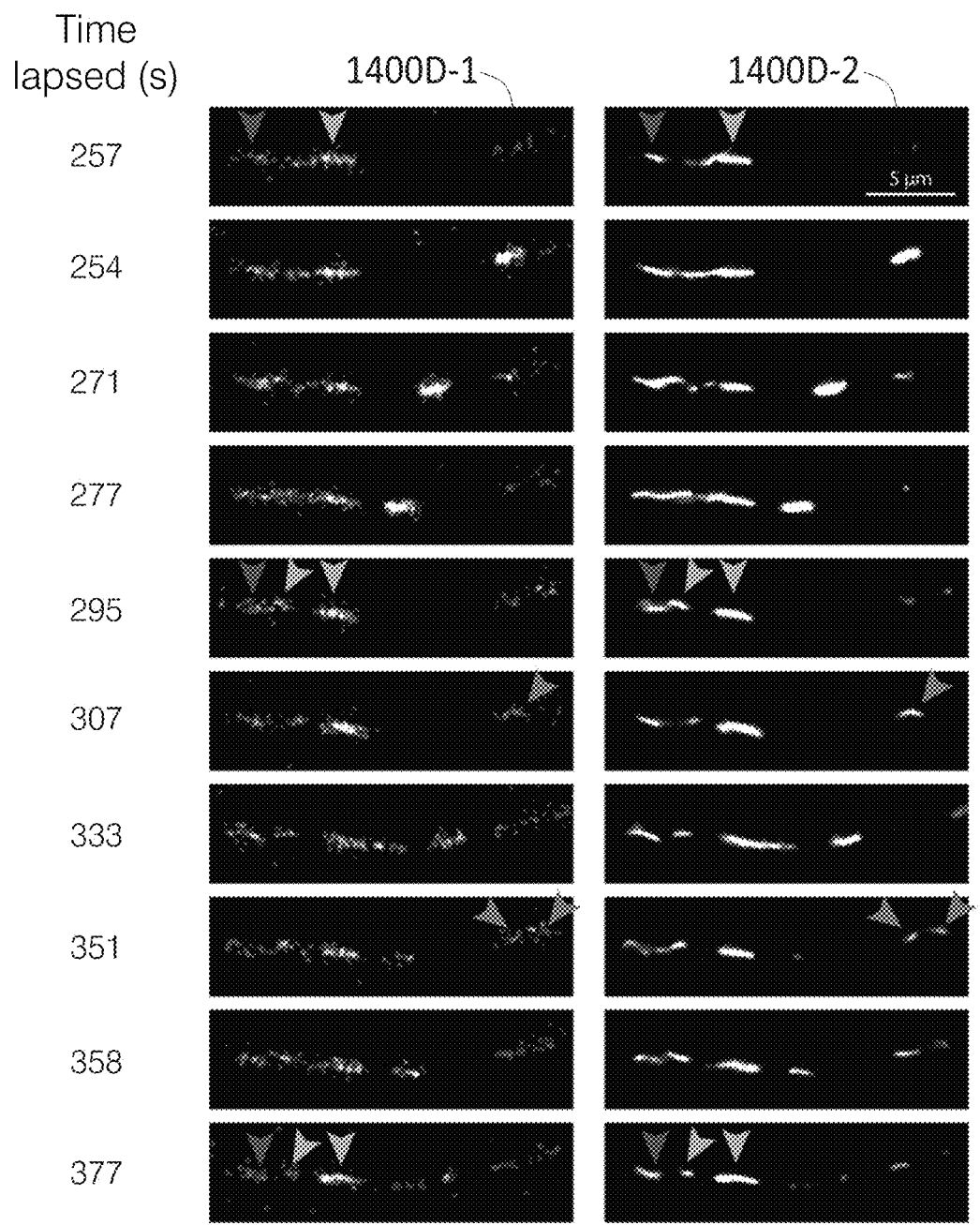

FIG. 14D illustrates images 1400D including LR image 1400D-1, and a synthetic HR image 1400D-2 (wherein the up sampling algorithm includes a PSSR model). Images 1400D illustrate still images of a number of mitochondria within a neuronal cytoplasm, at different moments in time. Images 1400D illustrate that because the collection of synthetic HR image 1400D-2 is 16× faster than HR-confocal imaging, instantaneous motility details were preserved (e.g., better time resolution), whereas in LR image 1400D-1 they were lost.

Figure 14E:
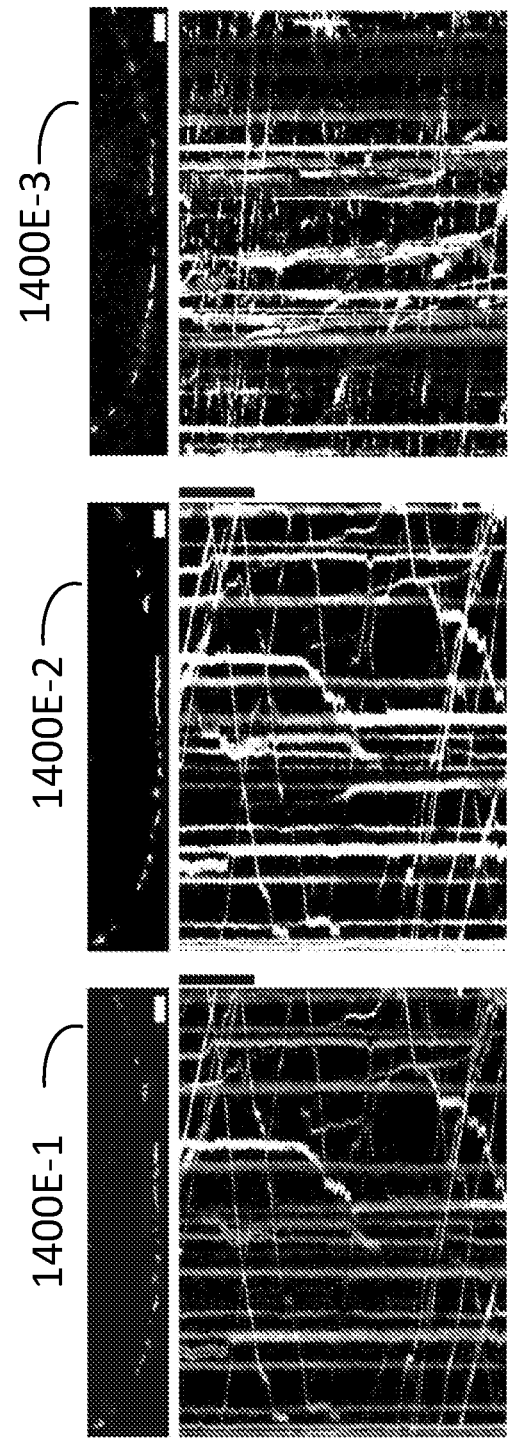

FIG. 14E illustrates images 1400E including LR image 1400E-1, a synthetic HR image 1400E-2 (wherein the up sampling algorithm includes a transfer-learning PSSR model, hereinafter referred to as "PSSR-TL model"), and a collected HR image 1400E-3 (e.g., imaging instrumentation operating in high-resolution mode, or GT image). The PSSR-TL model includes a pretrained PSSR model modified to use features of previously stored PSSR models for similar, or related applications (e.g., retrieved from annotated training database 252-3 or interaction history database 252-4). Images 1400E demonstrate that a PSSR-TL model as disclosed herein significantly improves the image quality compared to the original LR-image 1400E-1, and has even higher SNR than GT image 1400E-3. The image enhancement provided by a PSSR-TL model as disclosed herein enables resolution of two mitochondria moving past one another in the axon, as well as fission and fusion events. By comparing the richness of crossing traces in synthetic HR image 1400E-2 with the fainter and fewer crossing traces in GT image 1400E-3, it is clear that the PSSR-TL model is able to catch motility phenomena that even the GT technique misses.

Figure 14F:
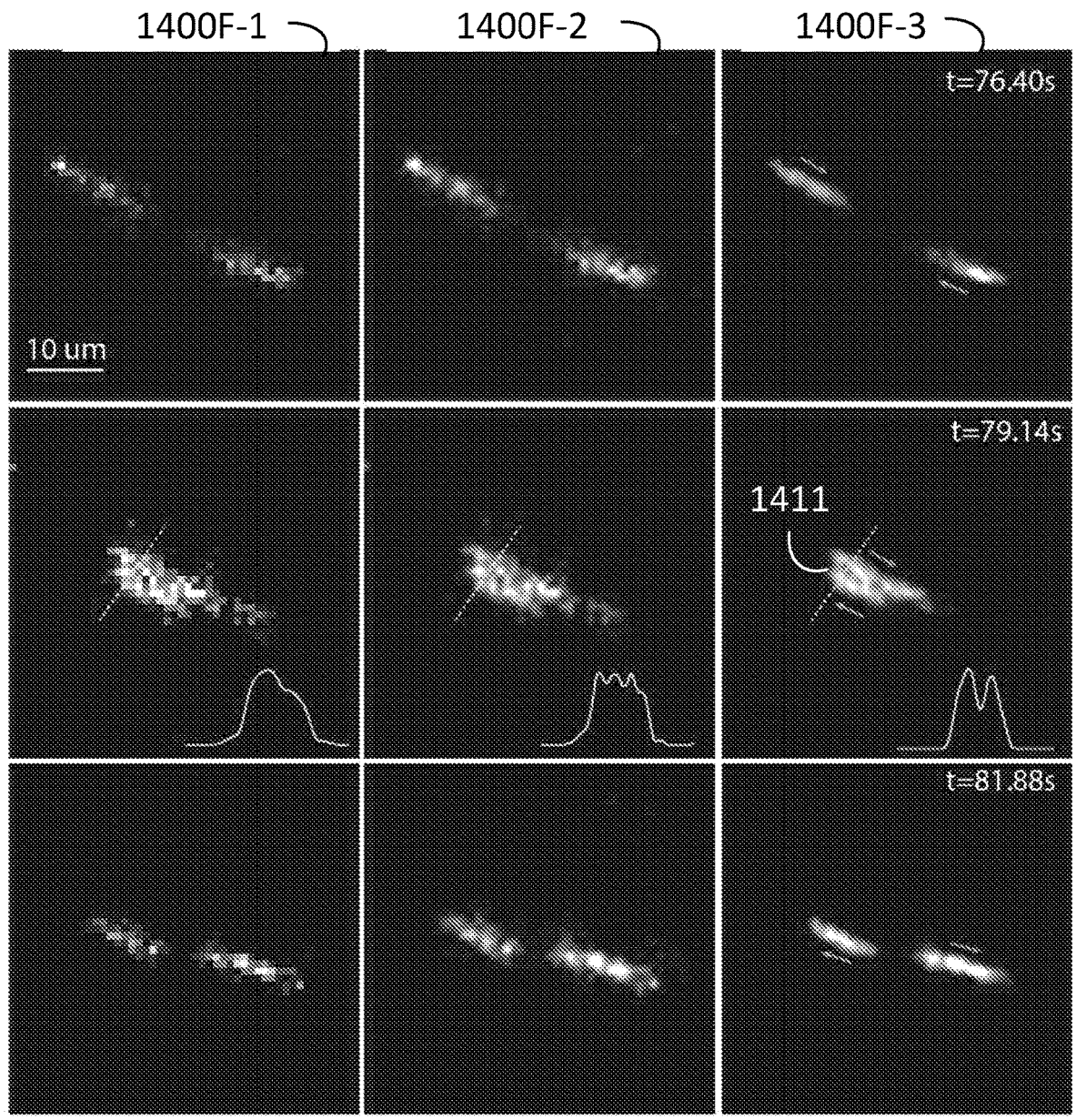

FIG. 14F illustrates images 1400F including LR image 1400E-1, a synthetic HR image 1400E-2 (wherein the up sampling algorithm includes a bilinear interpolation), and a synthetic HR image 1400E-3 (wherein the up sampling algorithm includes a PSSR-TL model). The improved speed, resolution, and SNR observed in images 1400E-3, enable detection of mitochondrial traffic events 1411 that were not detectable in the raw LR images. Each row of images 1400F corresponds to a different time during image collection.

Figure 14G:
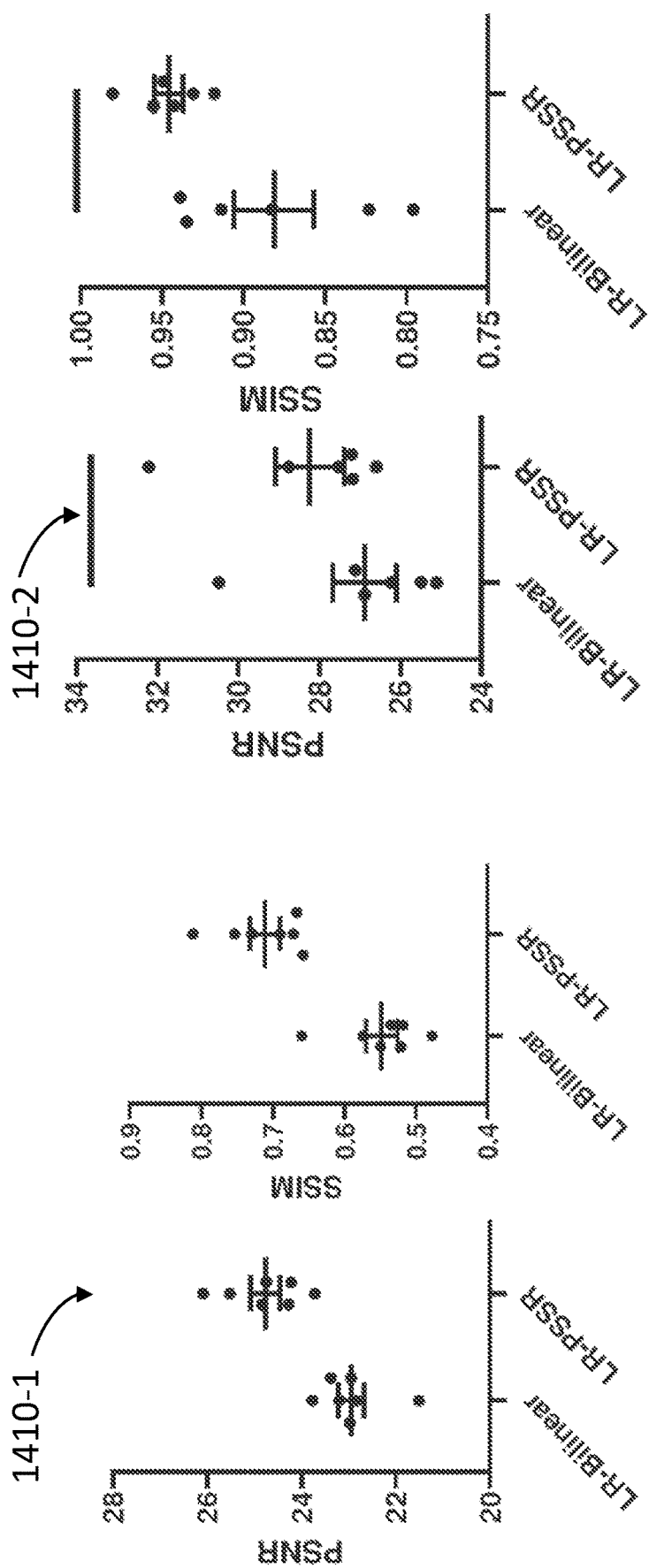

FIG. 14G illustrates image quality graphs 1410-1 and 1410-2 (hereinafter, collectively referred to as "graphs 1410") for multiple images 1400C after applying a PSSR-TL model for resolution enhancement. Graphs 1410-1 correspond to semi-synthetic pair 1401, and graphs 1410-2 correspond to real-world pairs 1402, both using the two image quality measures as disclosed herein (PSNR and SSIM). The improvement in image quality introduced by PSSR-TL is evident.

FIGS. 14H-14I illustrate charts 1420$h$ and 1420$i$ (hereinafter, collectively referred to as "charts 1420"), including a statistical analysis of mitochondrial motility results obtained from images 1400C, 1400D, and 1400E (cf. FIGS. 14C through 14E). Charts 1420 are separated by column according to whether the data pictured is collected from an LR image ("LR"), a synthetic HR image ("HR"), or a GT image ("GT"). Chart 1420$h$ illustrates a histogram of total distance traveled by the mitochondria (μm), and chart 1420$i$ illustrates a histogram of the measured velocity of the mitochondria (μm/s). Notably, the overall total distance mitochondria travelled in axons was the same for both LR-confocal and HR-confocal. In addition, the synthetic HR image indicates a much-varied distribution of mitochondrial velocities (e.g., a larger range), while the GT image shows almost no ability to measure velocity (with an average very close to zero).

Figure 14K:
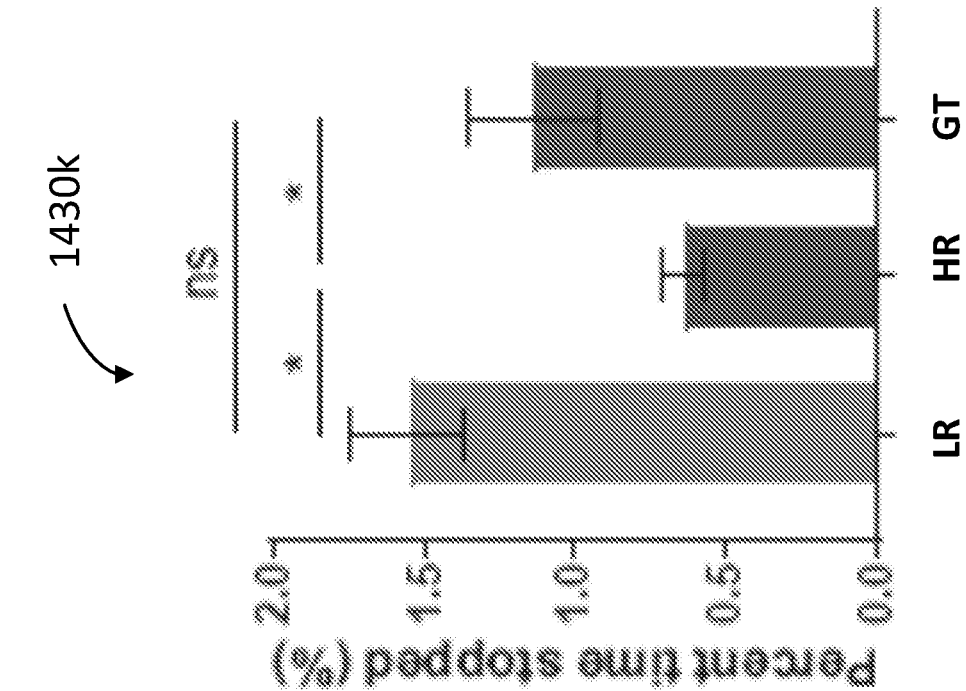
Figure 14J:
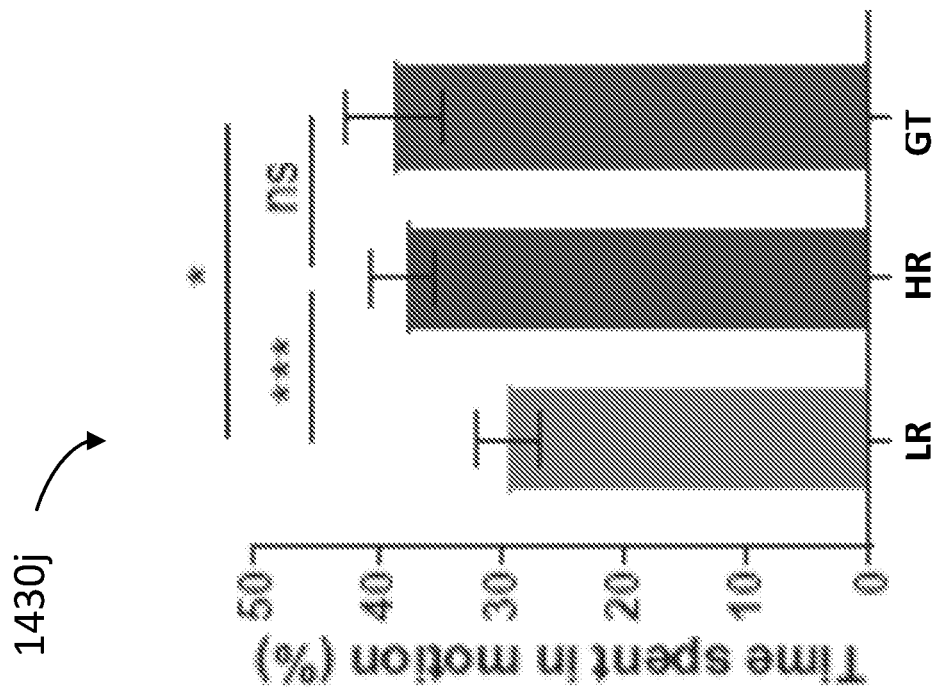

FIGS. 14J through 14K illustrate charts 1430$j$ and 1430$k$ (hereinafter, collectively referred to as "charts 1430"), including a statistical analysis of mitochondrial motility results obtained from images 1400C, 1400D, and 1400E (cf. FIGS. 14C through 14E). Charts 1430 are separated by column according to whether the data pictured is collected from an LR image ("LR"), a synthetic HR image ("HR"), or a GT image ("GT"). Chart 1430$j$ illustrates a histogram of the time spent in motion by the mitochondria (in percent, %), and chart 1430$k$ illustrates a complementary histogram of the time spent in the stopped position by the mitochondria (in percent, %). Small distances travelled were easy to define in the LR-PSSR-TL images, and therefore there was an overall reduction in the percent of time mitochondria spent in the stopped position in the LR-PSSR-TL data. Overall, LR-PSSR-TL and HR-confocal provided similar values for the percent time mitochondria spent in motion.

Figure 15:
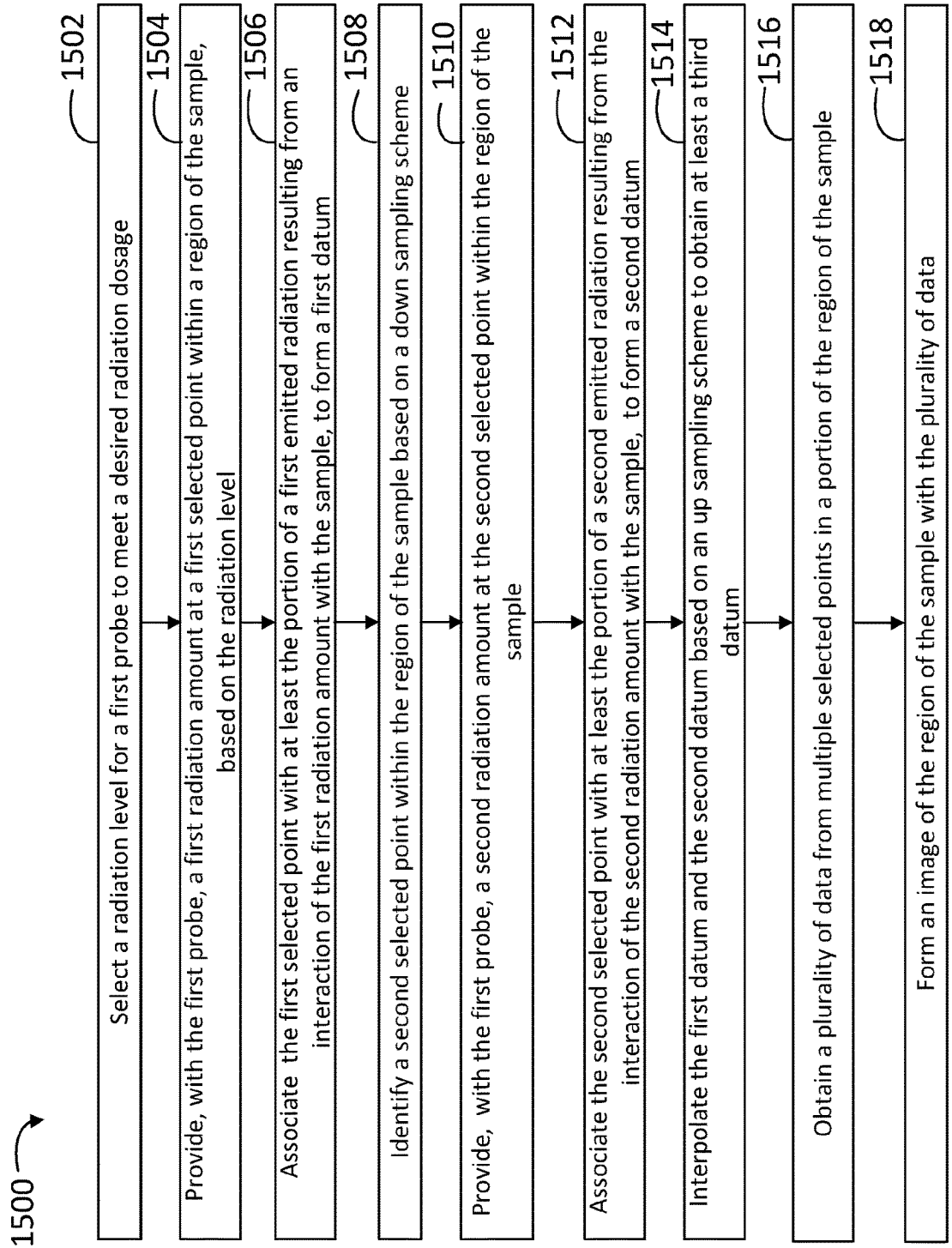
FIG. 15 illustrates steps in a method for controlling an imaging instrumentation to obtain an enhanced image, according to various embodiments.

FIG. 15 is a flow chart illustrating steps in a method for controlling an imaging instrumentation to obtain an enhanced image, according to various embodiments. Method 1500 may be performed by one or more control devices coupled with image instrumentation (e.g., control device 130 and image instrumentation 110, cf. FIGS. 1 and 2). For example, at least some of the steps in method 1500 may be performed by one component in a computer in the control device or an application in the image instrumentation (e.g., external interfaces 218, application 242, hardware driver 248, imaging hardware 246, probe 271 and detector 272, cf. FIG. 2). Accordingly, at least some of the steps in method 1500 may be performed by a processor executing commands stored in a memory of one or more computers and devices as disclosed herein (e.g., processors 212 and memories 220, cf. FIG. 2). The memory may also include a training database, an annotated training database, an image database, or an interaction history database storing data and information that may be used in one or more steps in method 1500 (e.g., databases 252, cf. FIG. 2). In some embodiments, the control device, the imaging instrumentation, and the database in method 1500 may be communicatively coupled via a network (e.g., network 150, cf. FIG. 1). Further, in various embodiments, at least some of the steps in method 1500 may be performed overlapping in time, almost simultaneously, or in a different order from the order illustrated in method 1500. Moreover, a method consistent with various embodiments disclosed herein may include at least one, but not all, of the steps in method 1500.

Step 1502 includes selecting a radiation level for a first probe to meet a desired radiation dosage.

In some embodiments, step 1502 includes preparing the sample prior to placing it in the imaging instrumentation. For example, in some embodiments, step 1502 may include growing cells in DMEM supplemented with 10% fetal bovine serum at 37° C. with 5% CO2. In some embodiments, step 1502 may include plating cells onto either 8-well #1.5 imaging chambers or #1.5 35 mm dishes (Cellvis), and coating the dishes with 10 µg/mL fibronectin in PBS at 37° C. for 30 minutes prior to plating. In some embodiments, step 1502 may include adding 50 nM MitoTracker Deep Red or CMXRos Red for 30 minutes, and washing the dish for at least 30 minutes to allow for recovery time before imaging in FluoroBrite media.

In some embodiments, step 1502 may include preparing a neuronal tissue sample. For example, in some embodiments, step 1502 includes preparing primary hippocampal neurons prepared from E18 rat (Envigo) embryos as previously described. In some embodiments, step 1502 includes dissecting hippocampal tissue from embryonic brain and further dissociating to a single hippocampal neuron by trypsinization with Papain. In some embodiments, step 1502 includes plating the prepared neurons on coverslips coated with 3.33 µg/mL laminin and 20 µg/mL poly-L-Lysine at a density of $7.5 \times 10^4$ cells/cm$^2$. In some embodiments, step 1502 includes maintaining the cells in Neurobasal medium supplemented with B27, penicillin/streptomycin, and L-glutamine for 7-21 days in vitro. In some embodiments, step 1502 includes transfecting the hippocampal neurons two days before imaging, with Lipofectamine 2000.

Step 1504 includes providing, with the first probe, a first radiation amount at a first selected point within a region of the sample, based on the radiation level.

Step 1506 associating the first selected point with at least the portion of a first emitted radiation resulting from an interaction of the first radiation amount with the sample, to form a first datum.

Step 1508 includes identifying a second selected point within the region of the sample based on a down sampling scheme.

Step 1510 includes providing, with the first probe, a second radiation amount at the second selected point within the region of the sample.

Step 1512 associating the second selected point with at least the portion of a second emitted radiation resulting from the interaction of the second radiation amount with the sample, to form a second datum.

Step 1514 includes interpolating the first datum and the second datum based on an up sampling scheme to obtain at least a third datum.

Step 1516 includes obtaining a plurality of data from multiple selected points in a portion of the region of the sample.

Step 1518 includes forming an image of the region of the sample with the plurality of data.

In some embodiments, step 1518 includes segmenting the image. For example, in some embodiments, step 1518 includes aligning rigid image sets generated from the same region of neuropil (LR-Bilinear; LR-PSSR; HR), identifying, and cropping presynaptic axonal boutons (n=10) from the image set. In some embodiments, step 1518 includes assigning randomly generated file names to the image sets from the three conditions, and distributing to two blinded human experts for manual counting of presynaptic vesicles. In some embodiments, step 1518 includes identifying vesicles by identifying a clear and complete membrane, being round in shape, and of approximately 35 nm in diameter. In some embodiments, step 1518 includes de-selecting, for consistency between human experts, vesicles that were embedded in or attached to obliquely sectioned, axonal membranes. In some embodiments, step 1518 includes counting docked and non-docked synaptic vesicles as separate pools. In some embodiments, step 1518 includes recording, unblinding, and grouping vesicle counts, by condition and by expert counter. In some embodiments, step 1518 includes conducting a linear regression analysis between the counts of the HR images and the corresponding images of the two different LR conditions (LR-bilinear; LR-PSSR), and determining how closely the counts corresponded between the HR and LR conditions. In some embodiments, step 1518 includes conducting a linear regression analysis to determine the variability between counters.

Figure 16:
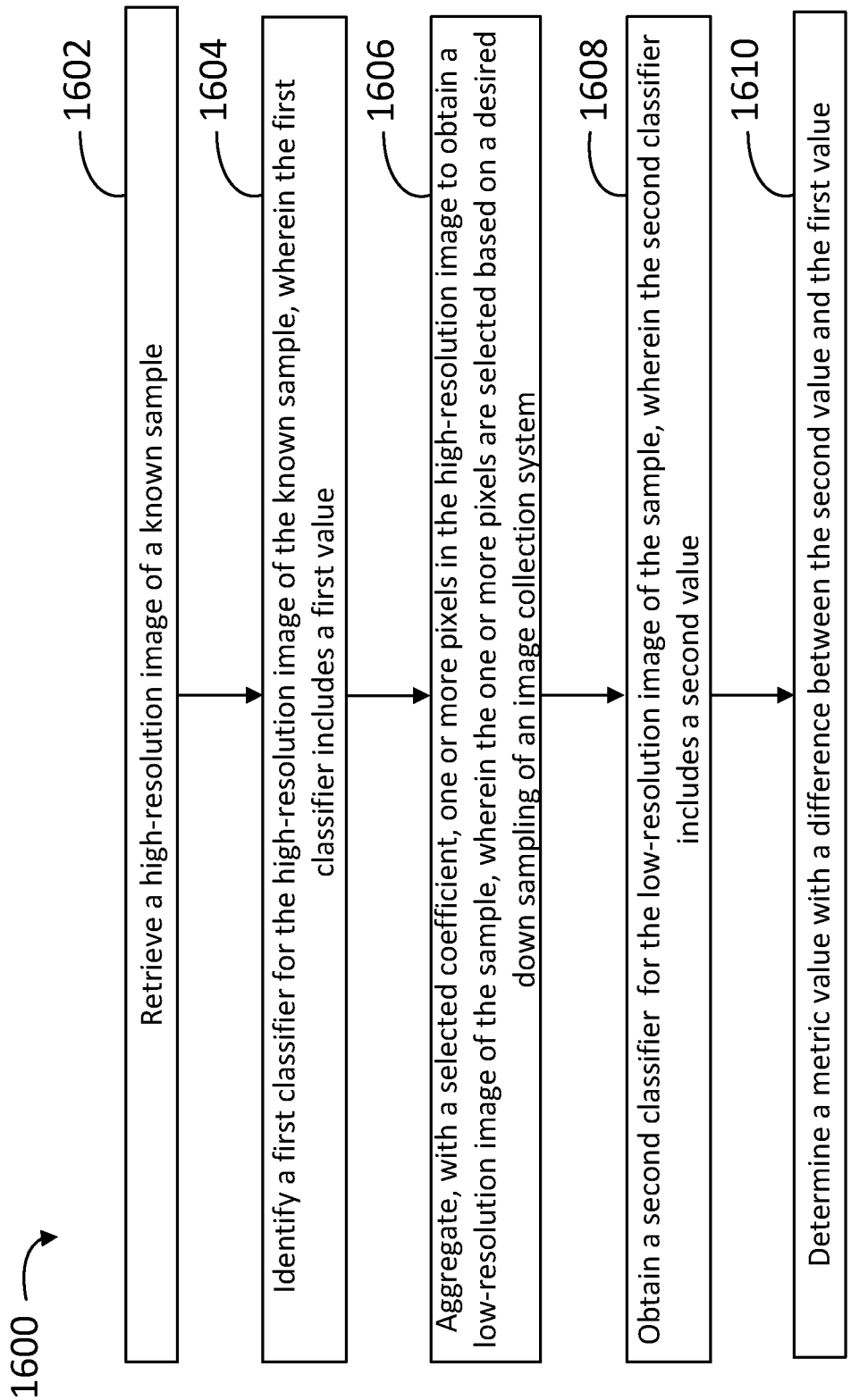
FIG. 16 illustrates steps in a method for training an algorithm to control imaging instrumentation to obtain an enhanced image, according to various embodiments.

FIG. 16 is a flow chart illustrating steps in a method for training an algorithm to control imaging instrumentation to obtain an enhanced image, according to various embodiments. Method 1600 may be performed by one or more control devices coupled with image instrumentation (e.g., control device 130 and image instrumentation 110, cf. FIGS. 1 and 2). For example, at least some of the steps in method 1600 may be performed by one component in a computer in the control device or an application in the image instrumentation (e.g., external interfaces 218, hardware driver 248, and application 242, cf. FIG. 2). Accordingly, at least some of the steps in method 1600 may be performed by a processor executing commands stored in a memory of one or more computers and devices as disclosed herein (e.g., processors 212 and memories 220, cf. FIG. 2). The memory may also include a training database, an annotated training database, an image database, or an interaction history database storing data and information that may be used in one or more steps in method 1600 (e.g., databases 252, cf. FIG. 2). In some embodiments, the control device, the imaging instrumentation, and the database in method 1600 may be communicatively coupled via a network (e.g., network 150, cf. FIG. 1). Further, in various embodiments, at least some of the steps in method 1600 may be performed overlapping in time, almost simultaneously, or in a different order from the order illustrated in method 1600. Moreover, a method consistent with various embodiments disclosed herein may include at least one, but not all, of the steps in method 1600.

Step 1602 includes retrieving a high-resolution image of a known sample.

In some embodiments, step 1602 includes collecting a confocal image of U2OS cells with a 63×1.4NA oil objective on a confocal system with an inverted stage and heated incubation system with 5% $CO_2$ control. In some embodiments, step 1602 includes directing, for both HR and LR images, a laser power of 2.5 µW and a pixel dwell time of 1.15 µs/pixel. In some embodiments, step 1602 includes acquiring HR-confocal images with a 2× Nyquist pixel size of 49 nm/pixel in SR mode (e.g., a virtual pinhole size of 2.5 AU), and processing the images using auto-filter settings. In some embodiments, step 1602 includes acquiring low-resolution confocal images (LR-confocal) with the same settings but with 0.5× Nyquist pixel size (196 nm/pixel).

In some embodiments, step 1602 includes retrieving neuronal mitochondria imaging and kymograph analysis. For example, in some embodiments, step 1602 includes imaging live-cell primary neurons using a confocal microscope enclosed in a temperature control chamber at 37° C. and 5% $CO_2$, using a 63× (NA 1.4) oil objective in SR-confocal mode (e.g., 2.5 AU virtual pinhole). In some embodiments, step 1602 includes, for LR imaging, acquiring images with a confocal PMT detector having a pinhole size of 2.5 AU at 440×440 pixels at 0.5× Nyquist (170 nm/pixel) every 270.49 ms using a pixel dwell time of 1.2 µs and a laser power ranging between 1-20 µW. In some embodiments, step 1602 includes acquiring HR images at 1764× 1764 pixels at 2× Nyquist (42.5 nm/pixel) every 4.33 s using a pixel dwell time of 1.2 µs and a laser power of 20 µW. In some embodiments, step 1602 includes collecting imaging data using software, and processing HR images using a confocal processing. In some embodiments, step 1602 includes analyzing time-lapse movies automatically.

In some embodiments, step 1602 includes retrieving HR STEM data. For this, in some embodiments, step 1602 includes preparing tissue from a perfused 7-month old male rat, cut from the left hemisphere, stratum radiatum of CA1 of the hippocampus. In some embodiments, step 1602 includes staining, embedding, and sectioning the tissue at 45 nm, and imaging tissue sections with a STEM detector with a 28 kV accelerating voltage and an extractor current of 102 µA (gun aperture 30 µm). In some embodiments, step 1602 includes acquiring images with a 2 nm pixel size and a field size of 24576×24576 pixels, having a working distance from the specimen to the final lens as 3.7 mm, and the dwell time as 1.2 µs.

For the testing and validation ground truth data sets, step 1602 may include acquiring paired LR and HR images of the adult mouse hippocampal dentate gyrus middle molecular layer neuropil from ultrathin sections (80 nm), collected on silicon chips and imaged in an SEM. In some embodiments, step 1602 includes collecting pairs of 4×4 µm images from the same region at pixel sizes of both 8 nm and 2 nm, and an SEM set at: 3 kV; dwell time, 5.3 µs; line averaging, 2; aperture, 30 µm; working distance, 2 mm.

Step 1604 includes identifying a first classifier for the high-resolution image of the known sample, wherein the first classifier includes a first value.

Step 1606 includes aggregating, with a selected coefficient, one or more pixels in the high-resolution image to obtain a low-resolution image of the sample, wherein the one or more pixels are selected based on a desired down sampling of an image collection system. In some embodiments, step 1606 includes image baselining. In some embodiments, step 1606 includes lowering the SNR of one or more pixel values in the HR image corresponding with the same field of view taken under the imaging instrumentation. In some embodiments, step 1606 includes collecting the HR image and the baseline image obtained in step 1606 to form an image pair for further training the algorithm. In some embodiments, step 1606 includes normalizing the high-resolution image from 0 to 1 before aggregating the pixel values (e.g., a 1000×1000 pixel image would be down sampled to 250×250 pixels in a 16× reduction factor). In some embodiments, step 1606 includes rescaling the aggregated pixel value to 8-bit format [0 to 255] for viewing with normal image analysis software. In some embodiments, step 1606 includes using spline interpolation of order 1 or more, for aggregating the pixel values.

Step 1608 includes obtaining a second classifier for the low-resolution image of the sample, wherein the second classifier includes a second value.

Step 1610 includes determining a metric value with a difference between the second value and the first value. In some embodiments, step 1610 includes selecting a metric threshold based on a desired image quality, and modifying the selected coefficient when a metric value surpasses the metric threshold. Step 1610 may further include storing the selected coefficient with a model for up sampling an image.

Computer System

Figure 17:
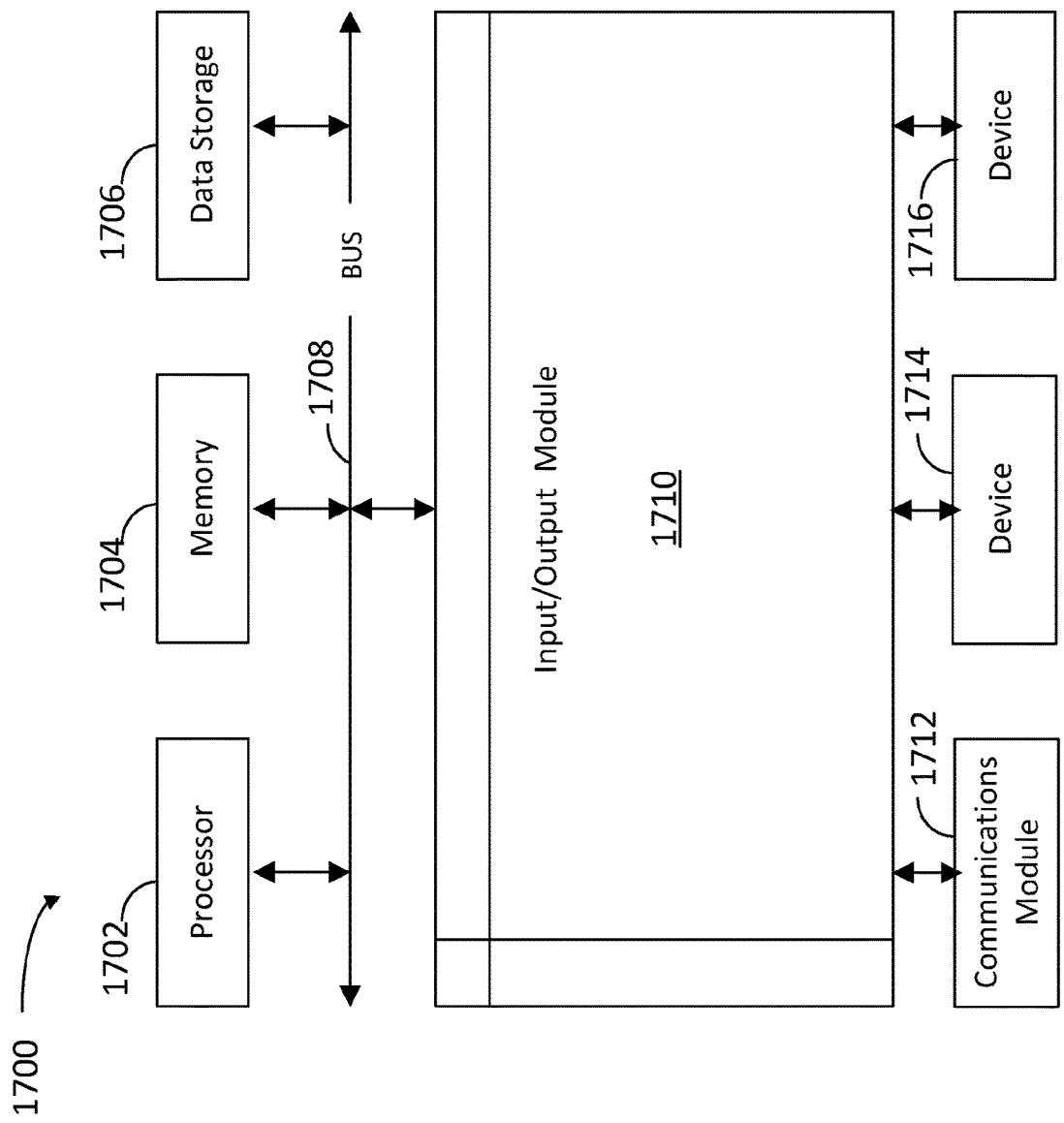
FIG. 17 illustrates a block diagram of a system configured to obtain an enhanced image from an imaging instrumentation, according to various embodiments.

FIG. 17 is a block diagram that illustrates a computer system 1700, upon which embodiments, or portions of the embodiments, of the present teachings may be implemented. In various embodiments of the present teachings, computer system 1700 can include a bus 1708 or other communication mechanism for communicating information, and a processor 1702 coupled with bus 1708 for processing information. In various embodiments, computer system 1700 can also include a memory 1704, which can be a random access memory (RAM) or other dynamic storage device, coupled to bus 1708 for determining instructions to be executed by processor 1702. Memory 1704 also can be used for storing temporary variables or other intermediate information during execution of instructions to be executed by processor 1702. In various embodiments, computer system 1700 can further include a read-only memory (ROM) or other static data storage device 1706 coupled to bus 1708 for storing static information and instructions for processor 1702. A storage device 1706, such as a magnetic disk or optical disk, can be provided and coupled to bus 1708 for storing information and instructions.

In various embodiments, computer system 1700 can be coupled via bus 1708 and input/output module 1710 to a display 1716, such as a cathode ray tube (CRT) or liquid crystal display (LCD), for displaying information to a computer user. An input device 1714, including alphanumeric and other keys, can be coupled to input/output module 1710 for communicating information and command selections to processor 1702. Another type of user input device 1714 is a cursor control, such as a mouse, a trackball, or cursor direction keys for communicating direction information and command selections to processor 1702 and for controlling cursor movement on display 1716. This input device 1714 typically has two degrees of freedom in two axes, a first axis (e.g., x) and a second axis (e.g., y), that allows the device to specify positions in a plane. However, it should be understood that input devices 1714 allowing for 3-dimensional (x, y, and z) cursor movement are also contemplated herein. A communications module 1712 may also be coupled with input/output module 1710, and configured to communicate with an external device or network (e.g., via a modem, Ethernet card, Wi-Fi antenna, RF antenna, and the like).

Consistent with certain implementations of the present teachings, results can be provided by computer system 1700 in response to processor 1702 executing one or more sequences of one or more instructions contained in memory 1704. Such instructions can be read into memory 1704 from another computer-readable medium or computer-readable storage medium, such as storage device 1706. Execution of the sequences of instructions contained in memory 1704 can cause processor 1702 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1702 for execution. Such a medium can take many forms, including but not limited to, non-volatile media, volatile media, and transmission media. Examples of non-volatile media can include, but are not limited to, optical, solid state, and magnetic disks, such as data storage device 1706. Examples of volatile media can include, but are not limited to, dynamic memory, such as memory 1704. Examples of transmission media can include, but are not limited to, coaxial cables, copper wire, and fiber optics, including the wires that include bus 1708.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can be read.

In addition to a computer-readable medium, instructions or data can be provided as signals on transmission media included in a communications apparatus or system to provide sequences of one or more instructions to processor 1702 of computer system 1700 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein including flow charts, diagrams, and the accompanying disclosure can be implemented using computer system 1700 as a standalone device or on a distributed network of shared computer processing resources such as a cloud computing network.

In accordance with various embodiments, the systems and methods described herein can be implemented using computer system 1700 as a standalone device or on a distributed network of shared computer processing resources such as a cloud computing network. As such, a non-transitory computer-readable medium can be provided in which a program is stored for causing a computer to perform the disclosed methods for identifying mutually incompatible gene pairs.

It should also be understood that the preceding embodiments could be provided, in whole or in part, as a system of components integrated to perform the methods described. For example, in accordance with various embodiments, the methods described herein can be provided as a system of components or stations for analytically determining novelty responses.

In describing the various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments. Similarly, any of the various system embodiments may have been presented as a group of particular components. However, these systems should not be limited to the particular set of components, their specific configuration, communication, and physical orientation with respect to each other. One skilled in the art should readily appreciate that these components can have various configurations and physical orientations (e.g., wholly separate components, units, and subunits of groups of components, and different communication regimes between components).

Although specific embodiments and applications of the disclosure have been described in this specification (including the associated Appendix), these embodiments and applications are exemplary only, and many variations are possible.

Recitation of Embodiments

A. A method for collecting an image from a sample includes selecting a radiation level for a first probe to meet a desired radiation dosage. The method also includes providing, with the first probe, a first radiation amount at a first selected point within a region of the sample, based on the radiation level, and associating the first selected point with at least the portion of a first emitted radiation resulting from an interaction of the first radiation amount with the sample, to form a first datum. The method also includes identifying a second selected point within the region of the sample based on a down sampling scheme, providing, with the first probe, a second radiation amount at the second selected point within the region of the sample, and associating the second selected point with at least the portion of a second emitted radiation resulting from the interaction of the second radiation amount with the sample, to form a second datum. The method also includes interpolating the first datum and the second datum based on an up sampling scheme to obtain at least a third datum, obtaining a plurality of data from multiple selected points in a portion of the region of the sample, and forming an image of the region of the sample with the plurality of data.

B. A system for collecting an image from a sample, includes a first probe configured to deliver a radiation to a selected point in the sample, a first detector configured to measure a scattered radiation resulting from an interaction between the radiation and the sample, a memory storing instructions and one or more processors configured to execute the instructions. When executing the instructions, the one or more processors cause the system to select a radiation level for a first probe to meet a desired radiation dosage, to provide, with the first probe, a first radiation amount at a first selected point within a region of the sample, based on the radiation level, and to associate the first selected point with at least the portion of a first emitted radiation resulting from an interaction of the first radiation amount with the sample, to form a first datum. The one or more processors also cause the system to identify a second selected point within the region of the sample based on a down sampling scheme, to provide, with a first probe, a second radiation amount at the second selected point within the region of the sample, and to associate the second selected point with at least the portion of a second emitted radiation resulting from the interaction of the second radiation amount with the sample, to form a second datum. The one or more processors also cause the system to interpolate the first datum and the second datum based on an up sampling scheme to obtain at least a third datum, to obtain a plurality of data from multiple selected points in a portion of the region of the sample, and to form an image of the region of the sample with the plurality of data.

C. A computer-implemented method to train an algorithm for collecting an image of a sample includes retrieving a high-resolution image of a known sample and identifying a first classifier for the high-resolution image of the known sample, wherein the first classifier includes a first value. The computer implemented method also includes aggregating, with a selected coefficient, one or more pixels in the high-resolution image to obtain a low-resolution image of the sample, wherein the one or more pixels are selected based on a desired down sampling of an image collection system, and obtaining a second classifier for the low-resolution image of the sample, wherein the second classifier includes a second value. The computer-implemented method also includes determining a metric value with a difference between the second value and the first value, modifying the selected coefficient when the metric value is at least equal to a selected metric threshold, and storing the selected coefficient with a model for up sampling an image obtained with the image collection system when the metric value is smaller than the selected metric threshold.

Each of embodiments A, B or C may be combined with the following elements in any number and order, to produce further embodiments consistent with the present disclosure, as follows:

Element 1, wherein selecting a radiation level for the first probe further includes selecting a dwell time and a resolution, and modifying at least one parameter from a group consisting of the dwell time, the resolution, and the radiation level, prior to forming the image of the region of the sample to meet a threshold quality of the image of the region of the sample. Element 2, wherein the first probe is an electron gun, and selecting a radiation level includes selecting a voltage and a current for the electron gun. Element 3, with the first probe, a second radiation amount at the second selected point within the region of the sample includes selecting a point within a distance from the first selected point to meet a minimum resolution allowed by the down sampling scheme and to meet a quality threshold value of the image of the region of the sample. Element 4, wherein providing, with the first probe, a second radiation amount at the second selected point within the region of the sample includes increasing a radiation level in the second radiation amount when a predicted quality of the image of the region of the sample is below a threshold quality value. Element 5, wherein providing, with the first probe, a second radiation amount to a second selected point within the region of the sample includes increasing a radiation level in the second radiation amount when a predicted quality of the image of the region of the sample is above a threshold quality value. Element 6, wherein the first probe is an electron gun, the plurality of data includes a scattered electron flux, the down sampling scheme is obtained from a training data collected from a confocal fluorescence image, and providing, with the first probe, a second radiation amount to a second selected point includes selecting a location of the second selected point based on a correlation between the confocal fluorescence image with a location of first selected point. Element 7, wherein interpolating the first datum and the second datum includes fitting a bilinear function to the first datum and the second datum. Element 8, wherein forming an image of the region of the sample with the plurality of data includes modifying at least a location or a signal amplitude value from one of the plurality of data to meet a quality threshold value of the image of the region of the sample. Element 9, wherein forming an image of the region of the sample with the plurality of data includes modifying at least a location or a signal amplitude value from multiple data in the plurality of data to meet a quality threshold value of the image of the region of the sample. Element 10, wherein forming an image of the region of the sample with a plurality of data includes correlating at least some of the plurality of data with a training data set. Element 11, wherein forming an image of the region of the sample with a plurality of data includes matching, through a correlation, the image of the region of the sample with a region of the sample from another image in a training data set. Element 12, wherein forming an image of the region of the sample includes removing a noise component from the plurality of data, wherein the noise component is identified with a training data set that is used to select the down sampling scheme. Element 13, wherein forming an image of the region of the sample includes identifying a noise source with a training data set that is used to select the down sampling scheme, from a group consisting of a radiation level noise, a probe jitter noise, a detector noise, a scattering noise, and a thermal noise. Element 14, wherein the first probe is a laser scanning first probe and the plurality of data includes confocal fluorescence data, and forming an image of the region of the sample with a plurality of data includes convolving the plurality of data with a training data set obtained with an electron microscope at a higher resolution. Element 15, further including reducing a distance between the second selected point and the first selected point when a predicted quality of the image of the region of the sample is below a desired quality threshold. Element 16, further including increasing a distance between the second selected point and the first selected point when a predicted quality of the image of the region of the sample is above a desired quality threshold. Element 17, the method further including determining a dwell time for collecting at least a portion of the first emitted radiation resulting from the interaction of the first radiation amount with the sample. Element 18, wherein the second selected point is approximately at a same location as the first selected point, further including forming the second datum at a selected time interval after forming the first datum, the method further including adding the image of the region of the sample to a time-lapse file. Element 19, further including selecting a time interval based on the down sampling scheme, forming the second datum at the time interval after forming the first datum, and identifying a physiological phenomenon in the region of the sample based on a similarity of the plurality of data with the physiological phenomenon in a training time-lapse file stored in a database. Element 20, further including selecting a time interval to collect a time-lapse plurality of data, identifying a physiological phenomenon from a difference between the plurality of data and the time-lapse plurality of data. Element 21, further including grouping at least a portion of the data by identifying an anatomic segment in the portion of the region of the sample, wherein the anatomic segment of the sample is at least a portion of one of: a blood vessel, a plant root, a cellular organelle, a neuronal axon, a brain, a neuronal synapse, a blood vessel, or a subcellular structure. Element 22, further including predicting an image quality value of the image based on the up sampling scheme before forming the image of the region of the sample with plurality of data, and reducing at least one of the radiation level or an image resolution when the image quality value of the image of the region is higher than a quality threshold. Element 23, wherein the sample is a living sample, the method further including collecting one or more images of the region of the sample at different times, to form a time-lapse file. Element 24, wherein the sample is a living sample, the method further including identifying a physiological phenomenon in the living sample when the up sampling scheme includes a plurality of data indicating a displacement of a component in the image of the region of the sample, and wherein the physiological phenomenon includes at least one of a mitochondrial fission, a mitochondrial displacement or a vesicular transition across a cellular membrane. Element 25, further including zooming in on a portion of the region of the sample and increasing an image resolution for the portion of the region of the sample. Element 26, further including determining a physiological information about the sample from a displacement in a component of the image of the region of the sample. Element 27, further including determining a physiological information about the sample with a statistical distribution of a velocity of a component of the image of the region of the sample. Element 28, further including determining multiple velocities of multiple components of the image of the region of the sample and identifying a physiological information about the sample when the velocities of multiple components fit an expected pattern.

Element 29, wherein at least some of the instructions in the memory include multiple coefficients in one of a neural network, a machine learning algorithm, or an artificial intelligence algorithm. Element 30, wherein the first probe includes an electron gun, the radiation is an electron flux, and the radiation level includes a voltage and a current of the electron flux. Element 31, wherein the first probe is a laser beam configured to operate in a continuous mode or in a pulsed mode according to the radiation level and a wavelength of the laser beam. Element 32, wherein the first probe includes a radiofrequency source, further including a first detector including a magnet configured to measure a decay of a resonant magnetization in the sample. Element 33, wherein the first probe includes a radioactive isotope embedded in the sample, further including a first detector including one of a gamma ray detector, a beta ray detector, or a positron detector. Element 34, further including a first detector including an anode configured to detect an electron beam scattered off a surface of the sample. Element 35, further including a first detector including an anode configured to detect an electron beam scattered through a bulk of the sample. Element 36, further including a first detector including an optical detector configured to measure a scattered radiation having a wavelength selected from a fluorescence spectrum of at least a portion of the sample. Element 37, further including a filter configured to separate the first radiation amount from the first probe from the first emitted radiation resulting from the interaction of the first radiation amount with the sample.

Element 38, wherein aggregating one or more pixels in the high-resolution image to obtain a low-resolution image of the sample includes using a bilinear interpolation function between a value for each of the one or more pixels in the high-resolution image. Element 39, wherein aggregating one or more pixels in the high-resolution image includes convolving the one or more pixels using the selected coefficient as a convolution factor. Element 40, wherein aggregating one or more pixels in the high-resolution image includes randomly injecting Gaussian additive noise to an aggregated pixel value. Element 41, wherein aggregating one or more pixels in the high-resolution image includes randomly injecting salt-and-pepper noise to an aggregated pixel value. Element 42, wherein aggregating one or more pixels in the high-resolution image includes increasing a signal-to-noise ratio of an aggregated pixel value. Element 43, wherein aggregating one or more pixels in the high-resolution image includes associating a baseline image including an aggregated pixel with the high-resolution image to form an image pair for further training the algorithm. Element 44, wherein aggregating one or more pixels in the high-resolution image includes interpolating multiple pixel values with a spline function of order of 1 or more. Element 45, wherein modifying the selected coefficient when the metric value is at least equal to a selected metric threshold includes transferring a value from one or more coefficients in one or more algorithms associated with a similar image of the sample into the selected coefficient. Element 46, further including modifying the selected coefficient according to a learning rate and determining the learning rate from an amount of weight update per iteration to arrive at optimal value. Element 47, further including obtaining a third classifier for the low-resolution image of the sample based on a second selected coefficient, the method further including modifying the second selected coefficient when the metric value is smaller than the selected metric threshold and storing the second selected coefficient when the metric value is at least equal to the selected metric threshold. Element 48, further including storing the high-resolution image and the low-resolution image, and the metric value as a training set. Element 49, further including selecting a second image from a second known sample, back-propagating the second image to obtain a back-propagated image, and modifying the selected coefficient when a second metric value is lower than the selected metric threshold, the second metric value being indicative of a difference between the back-propagated image and the second image. Element 50, further including determining a loss function based on a difference between the image of the known sample and a back-propagation image obtained with a reverse algorithm that is an inverse of the algorithm including the selected coefficient, and modifying the selected coefficient when the loss function has a value larger than a pre-selected threshold. Element 51, further including performing a backward pass to determine a contributing factor to a loss function that evaluates a difference between the image of a second known sample and a backpropagation image obtained with the selected coefficient. Element 52, further including updating a filter coefficient to improve a convolutional neural network. Element 53, further including selecting a lower learning rate and increasing the selected metric threshold. Element 54, further including weighting an internal covariate shift in a backpropagation of a second image of a second known sample when updating the selected coefficient. Element 55, further including selecting the metric value based on a peak signal-to-noise-ratio of the high-resolution image and a peak signal-to-noise ratio of a synthetic high-resolution image obtained from the low-resolution image and the second classifier. Element 56, further including calculating the metric value based on a structural similarity between the high-resolution image and a synthetic high-resolution image obtained from the low-resolution image and the second classifier.

What is claimed is:

1. A method for collecting an image from a cellular or tissue sample, comprising:
   selecting a radiation level for a first probe to meet a desired radiation dosage;
   providing, with the first probe, a first radiation amount at a first selected point within a region of the sample, based on the radiation level;
   associating the first selected point with at least the portion of a first emitted radiation resulting from an interaction of the first radiation amount with the sample, to form a first datum;
   identifying a second selected point within the region of the sample based on a down sampling scheme;
   providing, with the first probe, a second radiation amount at the second selected point within the region of the sample;
   associating the second selected point with at least the portion of a second emitted radiation resulting from the interaction of the second radiation amount with the sample, to form a second datum;
   interpolating the first datum and the second datum based on an up sampling scheme to obtain at least a third datum;
   obtaining a plurality of data from multiple selected points in a portion of the region of the sample; and
   forming an image of the region of the sample with the plurality of data.

2. The method of claim 1, wherein selecting a radiation level for the first probe further comprises selecting a dwell time and a resolution, and modifying at least one parameter from a group consisting of the dwell time, the resolution, and the radiation level, prior to forming the image of the region of the sample to meet a threshold quality of the image of the region of the sample.

3. The method of claim 1, wherein providing, with the first probe, a second radiation amount at the second selected point within the region of the sample comprises either increasing a radiation level in the second radiation amount when a predicted quality of the image of the region of the sample is below a threshold quality value, or decreasing a radiation level in the second radiation amount when a predicted quality of the image of the region of the sample is above a threshold quality value.

4. The method of claim 1, wherein the first probe is an electron gun, the plurality of data includes a scattered electron flux, the down sampling scheme is obtained from a training data collected from a confocal fluorescence image, and providing, with the first probe, a second radiation amount to a second selected point comprises selecting a location of the second selected point based on a correlation between the confocal fluorescence image with a location of first selected point.

5. The method of claim 1, wherein forming an image of the region of the sample with the plurality of data comprises modifying at least a location or a signal amplitude value from at least one of the plurality of data to meet a quality threshold value of the image of the region of the sample.

6. The method of claim 1, wherein forming an image of the region of the sample comprises identifying a noise source with a training data set that is used to select the down sampling scheme, from a group consisting of a radiation level noise, a probe jitter noise, a detector noise, a scattering noise, and a thermal noise.

7. The method of claim 1, further comprising reducing a distance between the second selected point and the first selected point when a predicted quality of the image of the region of the sample is below a desired quality threshold, or increasing a distance between the second selected point and the first selected point when a predicted quality of the image of the region of the sample is above a desired quality threshold.

8. The method of claim 1, the method further comprising determining a dwell time for collecting at least a portion of the first emitted radiation resulting from the interaction of the first radiation amount with the sample.

9. The method of claim 1, further comprising selecting a time interval based on the down sampling scheme, forming the second datum at the time interval after forming the first datum, and identifying a physiological phenomenon in the region of the sample based on a similarity of the plurality of data with the physiological phenomenon in a training time-lapse file stored in a database.

10. The method of claim 1, further comprising predicting an image quality value of the image based on the up sampling scheme before forming the image of the region of the sample with plurality of data, and reducing at least one of the radiation level or an image resolution when the image quality value of the image of the region is higher than a quality threshold.

11. The method of claim 1, wherein the sample is a living sample, the method further comprising identifying a physiological phenomenon in the living sample when the up sampling scheme includes a plurality of data indicating a displacement of a component in the image of the region of the sample, and wherein the physiological phenomenon comprises at least one of a mitochondrial fission, a mitochondrial displacement or a vesicular transition across a cellular membrane.

12. The method of claim 1, further comprising determining a physiological information about the sample from a displacement in a component of the image of the region of the sample, or with a statistical distribution of a velocity of a component of the image of the region of the sample.

13. A system for collecting an image from a cellular or tissue sample, comprising:
   a first probe configured to deliver a radiation to a selected point in the sample;
   a first detector configured to measure a scattered radiation resulting from an interaction between the radiation and the sample;
   a memory storing instructions; and
   one or more processors configured to execute the instructions and to cause the system to:
   select a radiation level for a first probe to meet a desired radiation dosage;
   provide, with the first probe, a first radiation amount at a first selected point within a region of the sample, based on the radiation level;

associate the first selected point with at least the portion of a first emitted radiation resulting from an interaction of the first radiation amount with the sample, to form a first datum;

identify a second selected point within the region of the sample based on a down sampling scheme;

provide, with a first probe, a second radiation amount at the second selected point within the region of the sample;

associate the second selected point with at least the portion of a second emitted radiation resulting from the interaction of the second radiation amount with the sample, to form a second datum;

interpolate the first datum and the second datum based on an up sampling scheme to obtain at least a third datum;

obtain a plurality of data from multiple selected points in a portion of the region of the sample; and form an image of the region of the sample with the plurality of data.

14. The system of claim 13, wherein the first probe comprises a radiofrequency source, further comprising a first detector including a magnet configured to measure a decay of a resonant magnetization in the sample.

15. The system of claim 13, wherein the first probe comprises a radioactive isotope embedded in the sample, further comprising a first detector including one of a gamma ray detector, a beta ray detector, or a positron detector.

16. The system of claim 13, further comprising a first detector including an anode configured to detect an electron beam scattered off a surface of the sample or through a bulk of the sample.

17. A computer-implemented method to train an algorithm for collecting an image of a cellular or tissue sample, comprising:

retrieving a high-resolution image of a known cellular or tissue sample;

identifying a first classifier for the high-resolution image of the known sample, wherein the first classifier includes a first value;

aggregating, with a selected coefficient, one or more pixels in the high-resolution image to obtain a low-resolution image of the sample, wherein the one or more pixels are selected based on a desired down sampling of an image collection system;

obtaining a second classifier for the low-resolution image of the sample, wherein the second classifier includes a second value;

determining a metric value with a difference between the second value and the first value;

modifying the selected coefficient when the metric value is greater than a threshold; and storing the selected coefficient with a model for up sampling an image when the metric value is smaller than the threshold.

18. The computer-implemented method claim 17, wherein aggregating one or more pixels in the high-resolution image comprises convolving the one or more pixels using the selected coefficient as a convolution factor.

19. The computer-implemented method of claim 17, wherein aggregating one or more pixels in the high-resolution image comprises randomly injecting Gaussian additive noise, or salt-and-pepper noise, to an aggregated pixel value.

* * * * *